US008541185B2

(12) United States Patent
Oved et al.

(10) Patent No.: US 8,541,185 B2
(45) Date of Patent: Sep. 24, 2013

(54) METHOD OF PREDICTING RESPONSIVENESS TO AUTOLOGOUS ADOPTIVE CELL TRANSFER THERAPY

(75) Inventors: Kfir Oved, Givataim (IL); Eran Eden, Haifa (IL); Martin Akerman, Haifa (IL); Roy Noy, Savyon (IL); Michal Besser, Tel-Aviv (IL); Yoram Reiter, Haifa (IL)

(73) Assignees: Technion Research & Development Foundation Limited, Haifa (IL); Tel HaShomer Medical Research Infrastructure and Services Ltd., Ramat-Gan (IL)

( * ) Notice: Subject to any disclaimer, the term of this patent is extended or adjusted under 35 U.S.C. 154(b) by 405 days.

(21) Appl. No.: 12/679,696

(22) PCT Filed: Sep. 15, 2008

(86) PCT No.: PCT/IL2008/001224
§ 371 (c)(1),
(2), (4) Date: Aug. 24, 2010

(87) PCT Pub. No.: WO2009/040789
PCT Pub. Date: Apr. 2, 2009

(65) Prior Publication Data
US 2010/0310534 A1     Dec. 9, 2010

Related U.S. Application Data

(60) Provisional application No. 61/064,268, filed on Feb. 25, 2008, provisional application No. 60/960,291, filed on Sep. 24, 2007.

(51) Int. Cl.
*G01N 33/574*     (2006.01)
*C12Q 1/02*     (2006.01)
*C12N 5/07*     (2010.01)

(52) U.S. Cl.
USPC ............ 435/7.23; 435/29; 435/325; 424/93.7

(58) Field of Classification Search
None
See application file for complete search history.

(56) References Cited

U.S. PATENT DOCUMENTS

| 7,205,157 | B2 * | 4/2007 | Jurgensen et al. ............ 436/177 |
| 8,287,857 | B2 * | 10/2012 | Dudley et al. ................ 424/93.7 |
| 2004/0009186 | A1 | 1/2004 | Bae et al. |
| 2006/0171949 | A1 | 8/2006 | Epstein et al. |

FOREIGN PATENT DOCUMENTS

WO    WO 2009/040789     4/2009

OTHER PUBLICATIONS

Office Action Dated Jan. 8, 2012 From the Israel Patent Office Re. Application No. 204666 and Its Translation Into English.
International Search Report Dated Apr. 21, 2009 From the International Searching Authority Re.: Application No. PCT/IL08/01224.
Invitation to Pay Additional Fees Dated Feb. 13, 2009 From the International Searching Authority Re.: Application No. PCT/IL08/01224.
Written Opinion Dated Apr. 21, 2009 From the International Searching Authority Re.: Application No. PCT/IL08/01224.
Besser et al. "Adoptive Cell Therapy for Metastatic Melanoma Patients: Pre-Clinical Development at the Sheba Medical Center", The Israel Medical Association Journal, IMAJ, XP002595987, 8(3): 164-168, Mar. 2006.
Brunner-Weinzierl et al. "Multiple Functions for CD28 and Cytotoxic T Lymphocyte Antigen-4 During Different Phases of T Cell Responses: Implications for Arthritis and Autoimmune Diseases", Arthritis Research & Therapy, 6(2): 45-54, 2004. Abstract.
Sheu et al. "Up-Regulation of Inhibitory Natural Killer Receptors CD94/NKG2A With Suppressed Intracellular Perforin Expression of Tumor-Infiltrating CD8+ T Lymphocytes in Human Cervical Carcinoma", Cancer Research, 65(7): 2921-2929, Apr. 1, 2005. Abstract, p. 2921, col. 2, Top §.
Response Dated Mar. 10, 2011 to Communication Pursuant to Rules 70(2) and 70a(2) EPC of Sep. 13, 2010 From the European Patent Office Re. Application No. 08789880.5.
Dudley et al. "Adoptive-Cell-Transfer Therapy for the Treatment of Patients With Cancer", Nature Reviews Cancer, 3: 666-676, Sep. 2003.
International Preliminary Report on Patentability Dated Apr. 1, 2010 From the International Bureau of WIPO Re.: Application No. PCT/IL2008/001224.
Supplementary European Search Report and the European Search Opinion Dated Aug. 25, 2010 From the European Patent Office Re. Application No. 08789880.5.
Filaci et al. "CD8+CD28− T Suppressor Lymphocytes Inhibiting T Cell Proliferative and Cytotoxic Functions Infiltrate Human Cancers", Clinical Immunology, XP022076792, 123: S112-S113, Jan. 1, 2007.
Oved et al. "Predicting and Controlling the Reactivity of Immune Cell Populations Against Cancer", Molecular Systems Biology, XP002595988, 5: , Apr. 2009.
Response Dated Aug. 24, 2011 to Communication Pursuant to Article 94(3) EPC of Apr. 27, 2011 From the European Patent Office Re. Application No. 08789880.5.

(Continued)

*Primary Examiner* — David M Naff

(57) ABSTRACT

A method of determining responsiveness to cancer treatment is disclosed. The method comprises analyzing a frequency of tumor infiltrating lymphocytes (TILs) having a $CD8^+CD28^-CD152^-$ signature in a sample of the subject, wherein a frequency of TILs having the $CD8^+CD28^-CD152^-$ signature above a predetermined level is indicative of a positive responsiveness to cancer treatment. Other signatures reflecting responsiveness to cancer treatment are also disclosed. In addition, methods of treating cancer based on these signatures are also disclosed.

3 Claims, 16 Drawing Sheets
(13 of 16 Drawing Sheet(s) Filed in Color)

(56) References Cited

OTHER PUBLICATIONS

Communication Pursuant to Article 94(3) EPC Dated Sep. 14, 2011 From the European Patent Office Re. Application No. 08789880.5.
Communication Pursuant to Rules 70(2) and 70a(2) EPC Dated Sep. 13, 2010 From the European Patent Office Re. Application No. 08789880.5.
Communication Under Rule 71(3) EPC Dated Sep. 27, 2012 From the European Patent Office Re. Application No. 08789880.5.
Response Dated Dec. 21, 2011 to Communication Pursuant to Article 94(3) EPC of Sep. 14, 2011 From the European Patent Office Re. Application No. 08789880.5.
Communication Pursuant to Article 94(3) EPC Dated Apr. 27, 2011 From the European Patent Office Re. Application No. 08789880.5.

\* cited by examiner

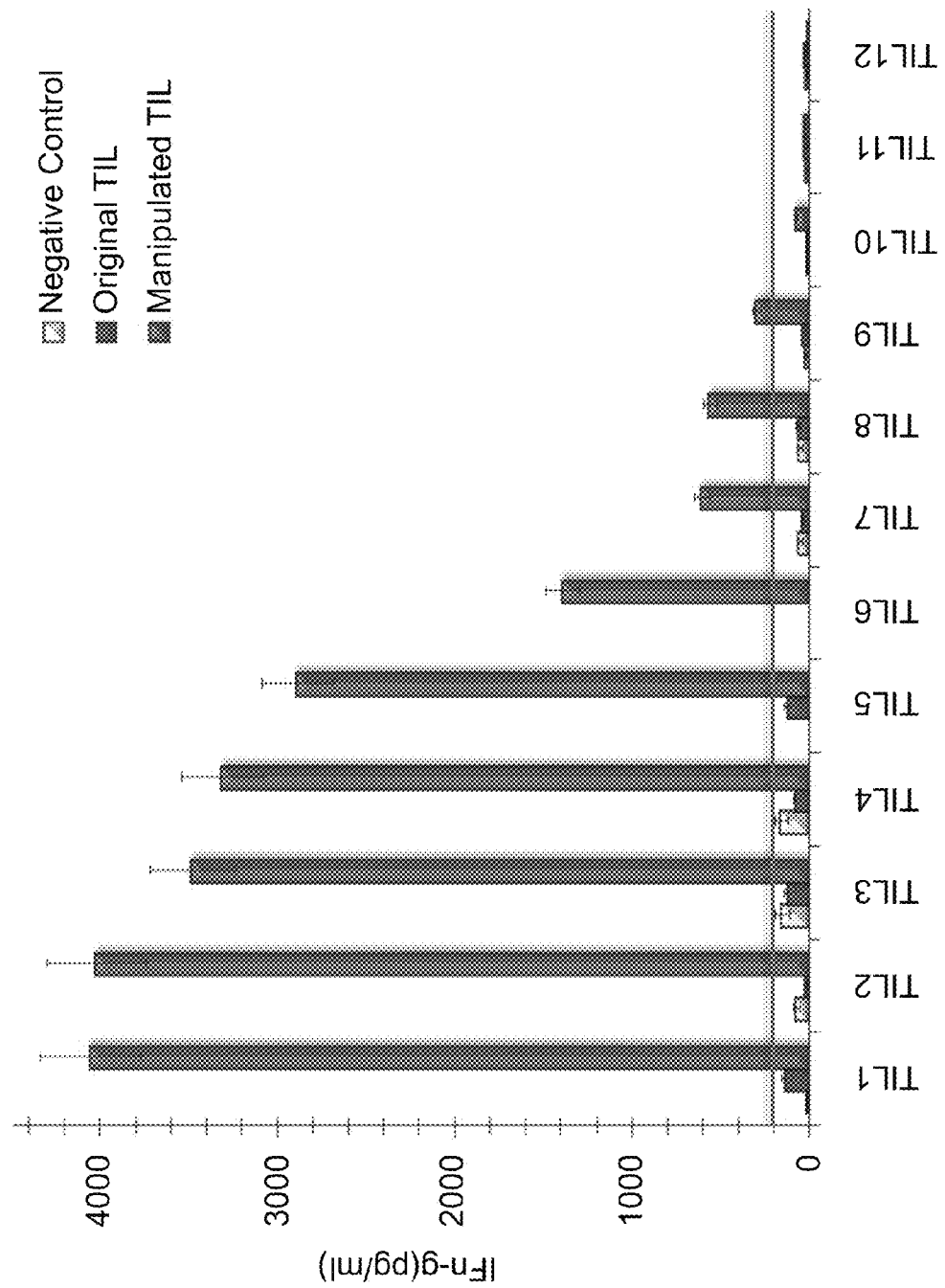

FIG. 5A

| Single staining |
|---|
| CD4+ |
| CD8+ |
| CD25+ |
| CD28+ |
| CD33+ |
| CD56+ |
| CD69+ |
| CD94+ |
| Gzm B |
| Perforin |

FIG. 5B

| Double staining |
|---|
| CD4+CD28+ |
| CD4+CD28- |
| CD4+CD56- |
| CD8+CD28- |
| CD8+CD56+ |
| CD8+CD56- |

FIG. 5C

| Triple staining |
|---|
| CD4+CD28-CD152- |
| CD4+CD28+CD152- |
| CD8+CD28-CD152- |
| CD4+CD33+CD69- |
| CD4+CD33+CD69+ |
| CD4+CD33-CD69- |
| CD4+CD33-CD69+ |
| CD8+CD33+CD69- |
| CD8+CD33+CD69+ |
| CD8+CD33-CD69- |
| CD8+CD33-CD69+ |
| CD4+CD25-CD56- |
| CD8+CD25-CD56+ |
| CD4+CD25+CD56- |
| CD8+CD25+CD56- |
| CD4+CD85-CD94- |
| CD8+CD85-CD94- |

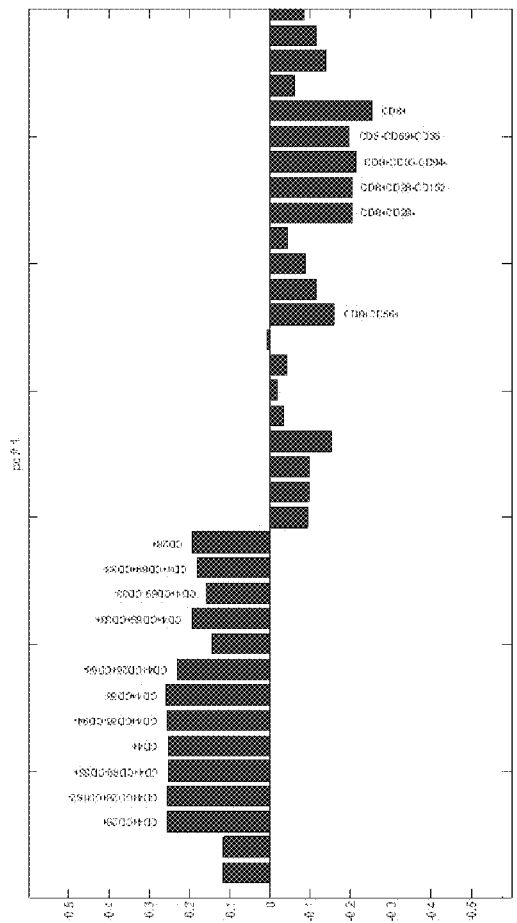
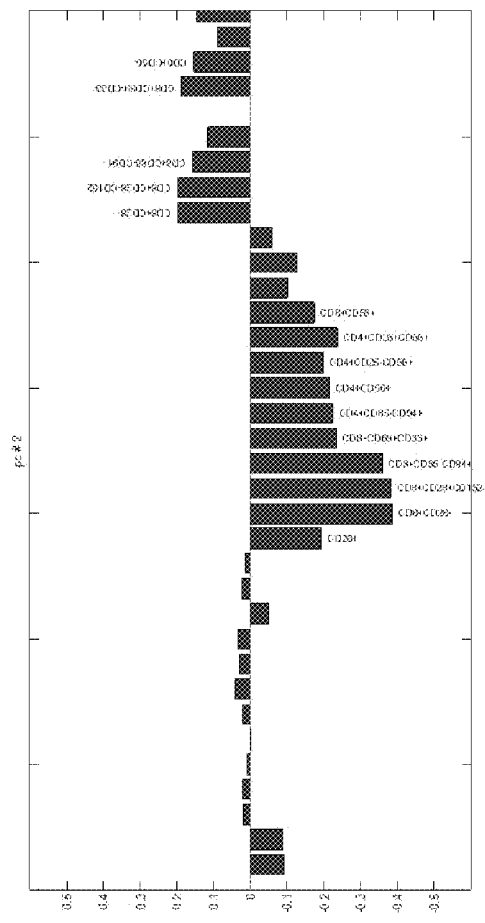
FIG. 11A
FIG. 11B

US 8,541,185 B2

METHOD OF PREDICTING RESPONSIVENESS TO AUTOLOGOUS ADOPTIVE CELL TRANSFER THERAPY

RELATED APPLICATIONS

This Application is a National Phase of PCT Patent Application No. PCT/IL2008/001224 having International filing date of Sep. 15, 2008, which claims the benefit of U.S. Provisional Patent Application Nos. 61/064,268 filed on Feb. 25, 2008 and 60/960,291 filed on Sep. 24, 2007. The contents of the above Applications are all incorporated herein by reference.

FIELD AND BACKGROUND OF THE INVENTION

The present invention, in some embodiments thereof, relates to T cell populations capable of treating cancer. Current therapeutic strategies focus predominantly on achieving the removal or death of cancer cells within the patient, through a diverse array of surgical and non-surgical techniques; the most widely used are chemotherapy and gamma irradiation. Those methods have a number of prominent disadvantages, in particular the culling of healthy cells/tissues within the patient, and the toxic side-effects of the current generation of chemotherapeutic drugs utilized in cancer treatment. Furthermore, these treatments are not always successful.

The spontaneous regression of certain cancers, such as melanoma or renal cell cancer, supports the idea that the immune system is sometimes capable of delaying tumor progression and on rare occasions eliminating a tumor altogether. These observations have led to research interest in a variety of immunologic therapies designed to stimulate the immune system.

Further evidence that an immune response to cancer exists in humans is provided by the existence of lymphocytes within melanoma deposits. These lymphocytes, when isolated, are capable of recognizing specific tumor antigens on autologous and allogeneic melanomas in an MHC restricted fashion. Tumor infiltrating lymphocytes (TILs) from patients with metastatic melanoma recognize shared antigens including melanocyte-melanoma lineage specific tissue antigens in vitro (Kawakami, Y., et al., (1993) J. Immunother. 14: 88-93; Anichini, A. et al., (1993) et al., J. Exp. Med. 177: 989-998). Anti-melanoma T cells appear to be enriched in TILs probably as a consequence of clonal expansion and accumulation at the tumor site in vivo (Sensi, M., et al., (1993) J. Exp. Med. 178:1231-1246).

The term adoptive immunotherapy describes the transfer of immunocompetent cells such as the TILs described herein above to the tumor-bearing host. Adoptive cell transfer (ACT) therapy for patients with cancer relies on the ex vivo generation of highly active tumor, specific lymphocytes, and their administration in large numbers to the autologous host.

Presently, ACT therapy however effectively treats only a limited number of patients. Preclinical models have identified a variety of ways to manipulate the host immune environment that increase ACT therapeutic efficacy. These include immunosuppression prior to cell administration and concurrent interleukin 2 administration with the transferred T cells.

Preclinical models have also identified characteristics of lymphocyte cultures that are required for successful ACT therapy. Until presently, the most important characteristic was thought to be the presence of high affinity, tumor antigen specific $CD8^+$ cells. It was also shown that $CD4^+$ cells were also required for effective treatment of some tumors [Surman et al, J. Immunology 164, 562-565, 2000]. In addition, it has been demonstrated that the presence of $CD4^+CD25^+$ T cells suppress autoimmunity and may be potent inhibitors of anti-tumor effects in mice [Shevach E. M. Nat. Rev. Immunol. 2, 389-400 (2002)]. This has led to the conclusion that lymphodepleting subpopulations comprising this signature may be beneficial for ACT therapy.

Some functional requirements of the cells for effective ACT were elucidated in animal models. For example, the secretion of IFN-γ by injected TILs was shown to significantly correlate with in vivo regression of murine tumors suggesting activation of T-cells by the tumor antigens (Barth, R. J., et al., (1991) J. Exp. Med. 173:647-658). Accordingly, selection of tumor-reactive T cells for adoptive immunotherapy may be effected by analyzing IFN-γ secretion following exposure to tumor antigens. Despite its clinical importance, little is known about the underlying composition and cellular interactions that determine the degree of TIL reactivity as measured by IFN-γ secretion and consequentially on how to control this reactivity.

SUMMARY OF THE INVENTION

According to an aspect of some embodiments of the present invention there is provided a method of determining responsiveness to cancer treatment in a subject in need thereof, the method comprising analyzing a frequency of tumor infiltrating lymphocytes (TILs) having a $CD8^+CD28^-CD152^-$ signature in a sample of the subject, wherein a frequency of TILs having the $CD8^+CD28^-CD152^-$ signature above a predetermined level is indicative of a positive responsiveness to cancer treatment.

According to some embodiments of the invention, the method further comprises analyzing a frequency of TILs having a $CD8^+CD69^+CD33^-$ signature in the TIL sample, wherein a frequency of TILs having the $CD8^+CD69^+CD33^-$ signature and the $CD8^+CD28^-CD152^-$ signature above a predetermined level is indicative of a negative responsiveness to cancer treatment.

According to an aspect of some embodiments of the present invention there is provided a method of determining responsiveness to cancer treatment in a subject in need thereof, the method comprising analyzing a frequency of TILs having a $CD8^+CD28^-CD152^-$ signature in a sample of the subject, wherein a frequency of TILs having a $CD8^+CD28^-CD152^-$ signature below a predetermined level is indicative of a negative responsiveness to cancer treatment.

According to some embodiments of the invention, the method further comprises analyzing a frequency of TILs having a $CD94^+$ signature in the sample, wherein a frequency of TILs not having the $CD8^+CD28^-CD152^-$ signature whilst having a CD94+ signature above a predetermined level is further indicative of a negative responsiveness to cancer treatment.

According to an aspect of some embodiments of the present invention there is provided a method of predicting T cell responsiveness to a cancer in a subject, comprising analyzing subpopulation marker signatures in a TIL sample of the subject, wherein a subpopulation marker signature corresponding to a reactive marker signatures as defined by FIG. 3A is indicative of T cell responsiveness and a subpopulation marker signature corresponding to a non-reactive marker signature as defined by FIG. 3A is indicative of a non T cell responsiveness.

According to some embodiments of the invention, the cancer treatment comprises adoptive transfer therapy.

According to an aspect of some embodiments of the present invention there is provided a method of treating cancer in a subject in need thereof, the method comprising depleting lymphocytes from a sample of TILs of the subject, wherein the lymphocytes express CD4, CD152 and CD28

According to some embodiments of the invention, the method further comprises depleting additional lymphocytes of the subject wherein the additional lymphocytes express CD85 and/or CD94.

According to an aspect of some embodiments of the present invention there is provided a method of treating cancer in a subject in need thereof, the method comprising enriching for a subpopulation of lymphocytes from a sample of TILs of the subject, the subpopulation expressing a $CD8^+ CD28^- CD152^-$ signature.

According to some embodiments of the invention, the method further comprises depleting an additional subpopulation of lymphocytes from the sample of $CD8^+CD28^-CD152^-$ enriched TILs, the additional subpopulation expressing a $CD8^+CD69^+CD33^-$ signature.

According to some embodiments of the invention, the subject has a cancer selected from the group consisting of prostate cancer, renal cell carcinoma, glioma and melanoma.

According to an aspect of some embodiments of the present invention there is provided a method of determining a reactivity of a subpopulation of TILs in a TIL sample, the method comprising:

(a) assaying an activity of a statistically significant number of TIL samples;

(b) analyzing the TIL samples by flow cytometry analysis of at least three markers per cell in order to classify subpopulations of cells, wherein at least one of the three markers is CD4 or CD8, at least a second of the three markers is a cytokine or chemokine and at least a third of the three markers is an adhesion molecule, a co-inhibitory receptor, a co-stimulatory receptor or a protein set forth in Table 5; and (c) analyzing a frequency of at least one subpopulation in the TIL sample, wherein a frequency above a predetermined threshold indicates that the at least one subpopulation of cells is associated with the activity.

According to some embodiments of the invention, the method further comprises removing the subpopulations following the analyzing the frequency, wherein a subpopulation comprising a frequency lower than 1% is removed.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying images. With specific reference now to the images in detail, it is stressed that the particulars shown are by way of example and for purposes of illustrative discussion of embodiments of the invention. In this regard, the description taken with the drawings makes apparent to those skilled in the art how embodiments of the invention may be practiced.

The patent or application file contains at least one drawing executed in color. Copies of this patent or patent application publication with color drawing(s) will be provided by the Office upon request and payment of the necessary fee.

In the drawings:

Figure 1A:
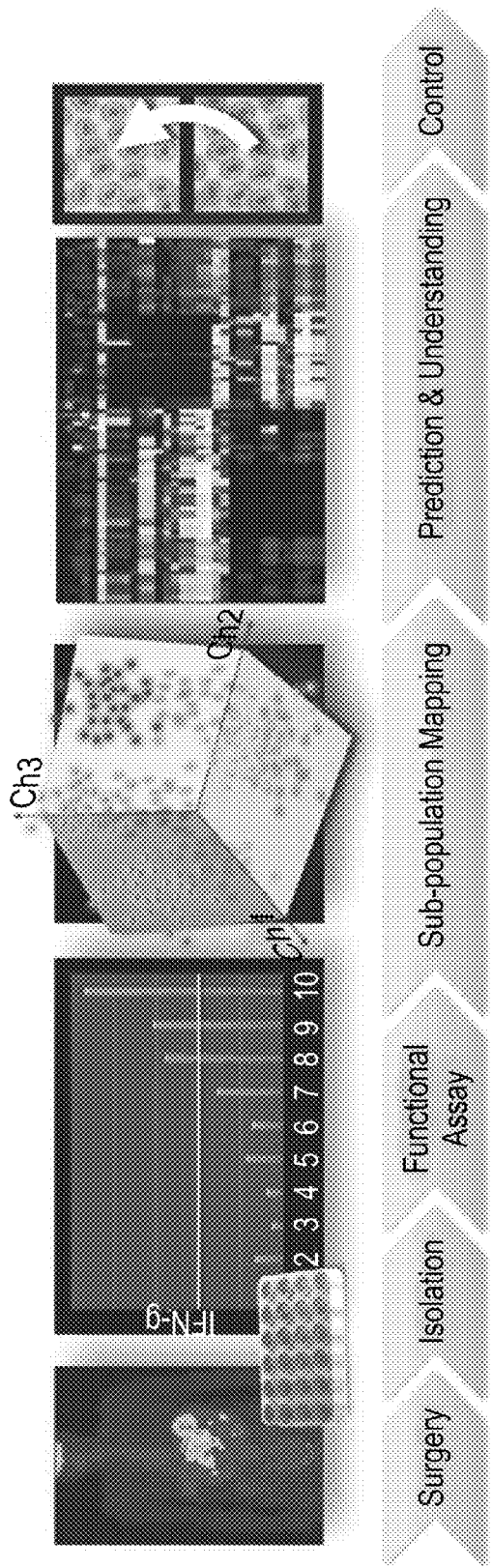

FIG. 1A is a schematic workflow of TIL characterization, analysis and reactivity control. As a first step TILs were extracted from surgically removed tumor mass originating from metastatic melanoma patients. Each TIL was characterized by functional evaluation of IFN-γ secretion levels followed by subpopulation fraction measurements using flow cytometry. This information was combined into a multi-parametric model for prediction and understanding of TIL reactivity. Following this analysis, the fractions of selected subpopulation were manipulated thus enabling controllability of TIL reactivity against melanoma.

Figure 1B:
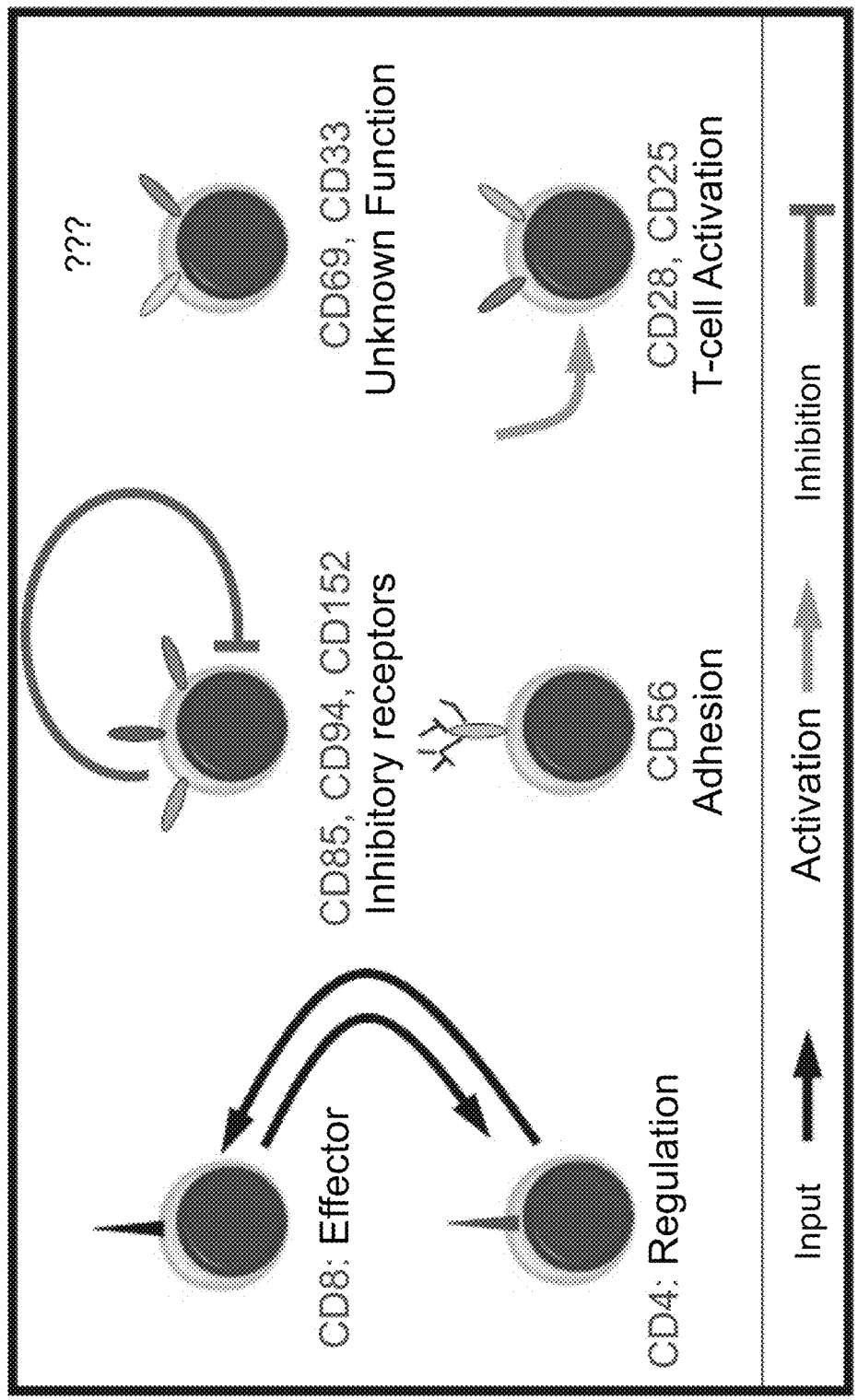

FIG. 1B is a diagram of the central cell surface receptors defining specific T-cell subpopulations with distinct functional states.

Figure 2:
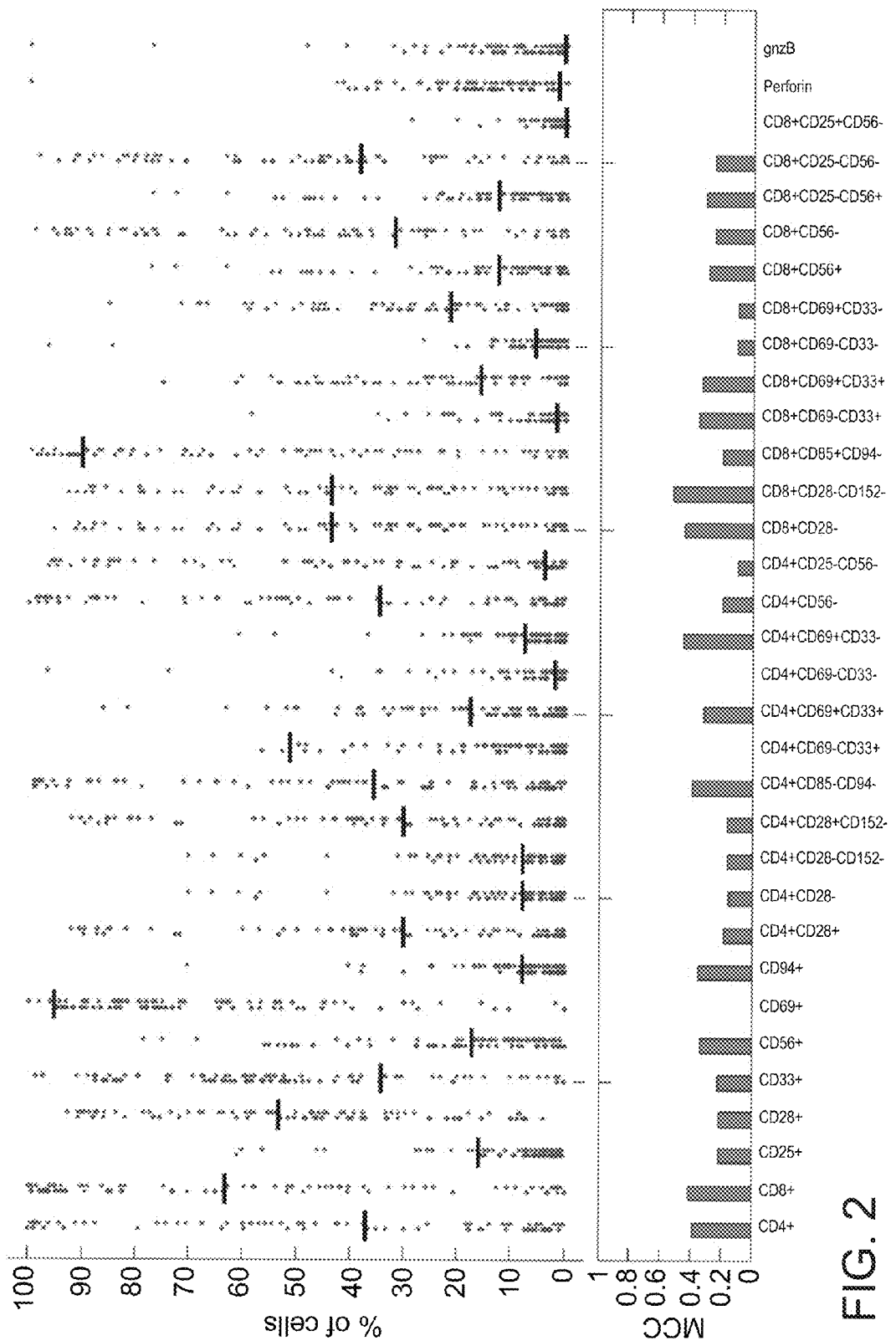

FIG. 2 are optimal cutoffs segregating reactive from nonreactive TILs as represented in a graphical form based on individual subpopulation fractions. For each subpopulation the blue and red dots indicate its fraction in 39 reactive and 52 nonreactive TILs respectively. Subpopulation based linear classification (using a leave five out testing scheme) produced MCCs in the range of 0 to 0.58. In general, MCC values range between −1 to +1 indicating completely wrong and perfect classification respectively. An MCC=0 indicates random. The black horizontal bars indicate the optimal border between reactive and nonreactive TILs as determined by MCC.

Figure 3A:
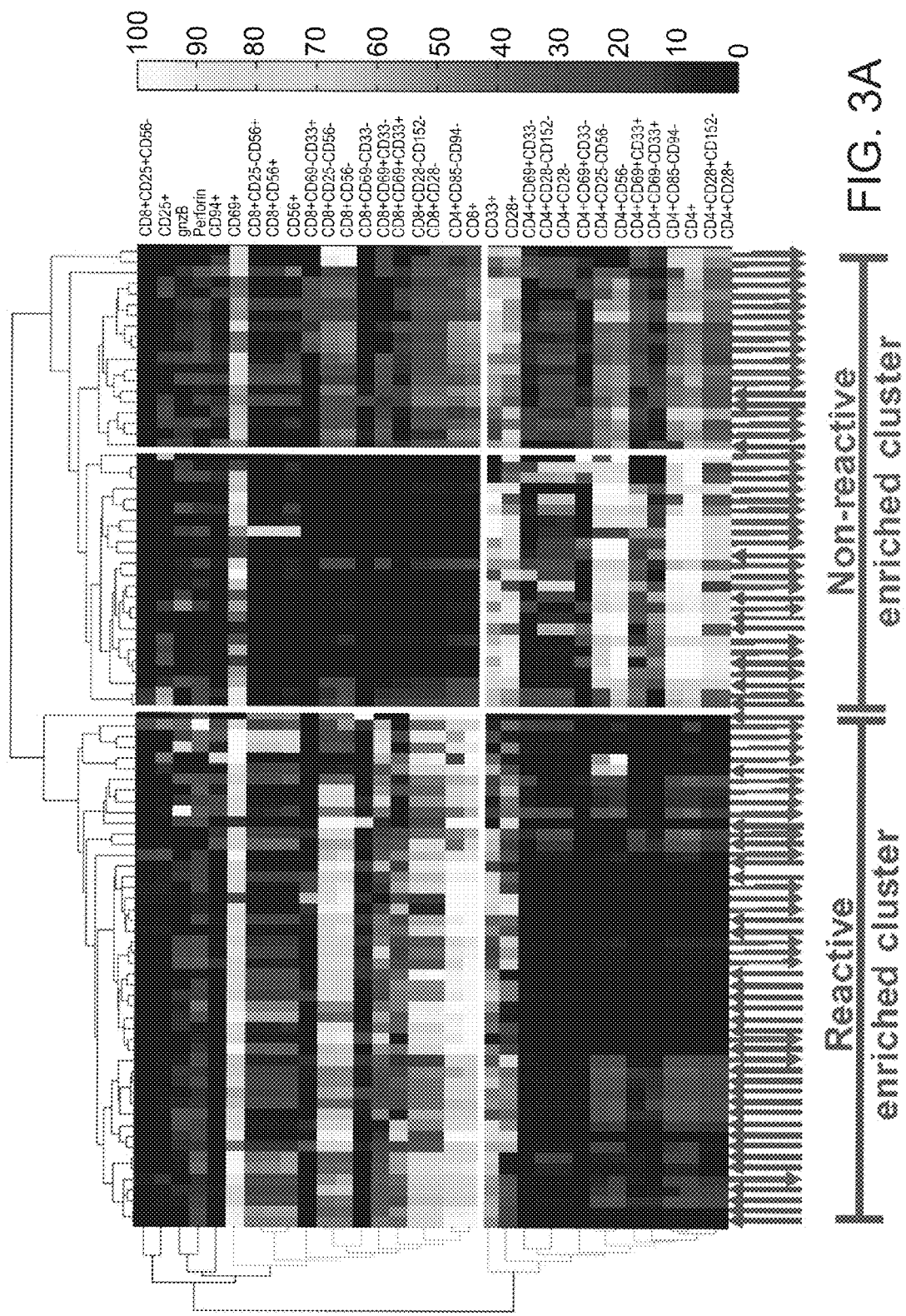
Figure 3B:
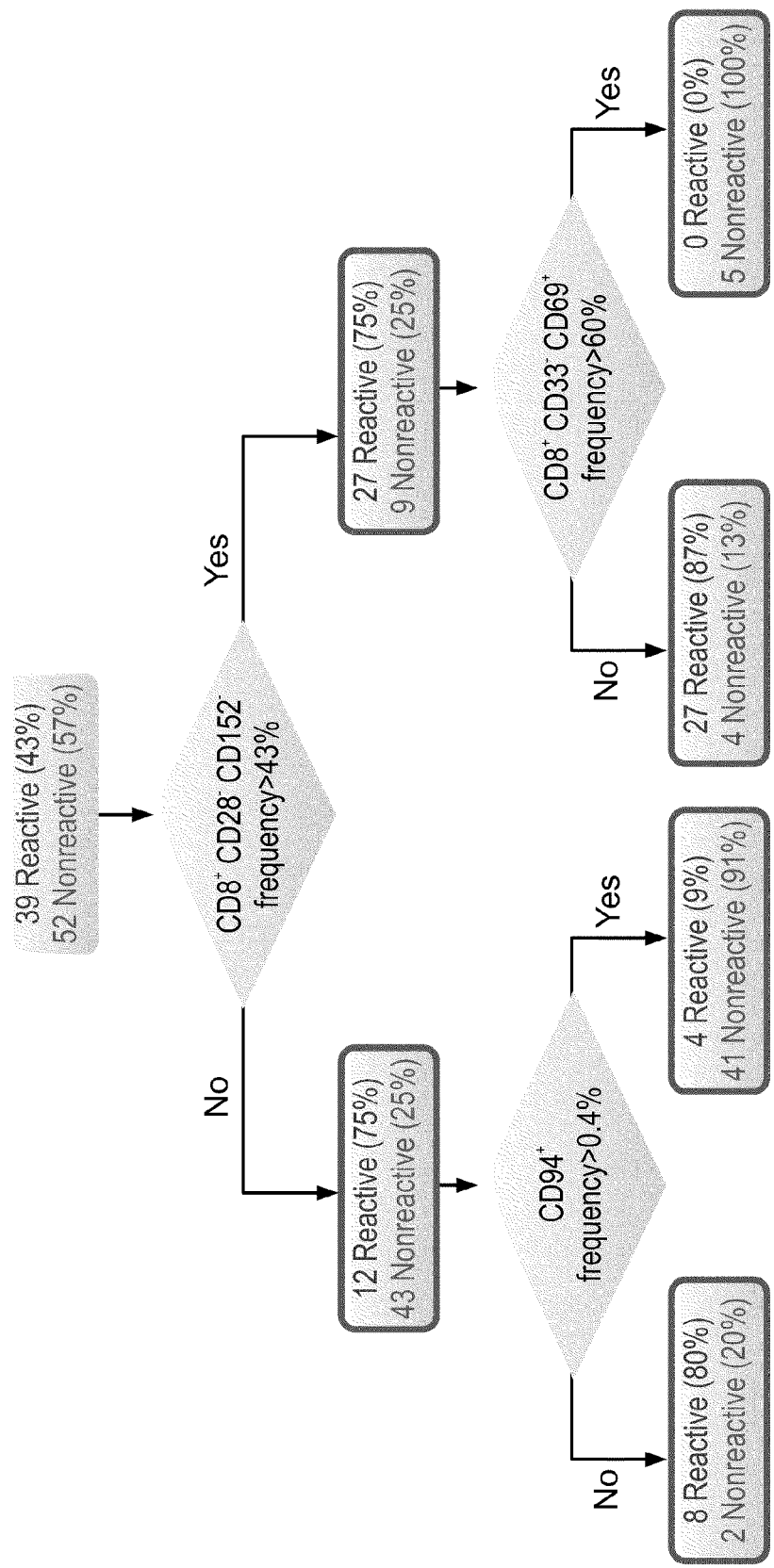
Figure 3C:
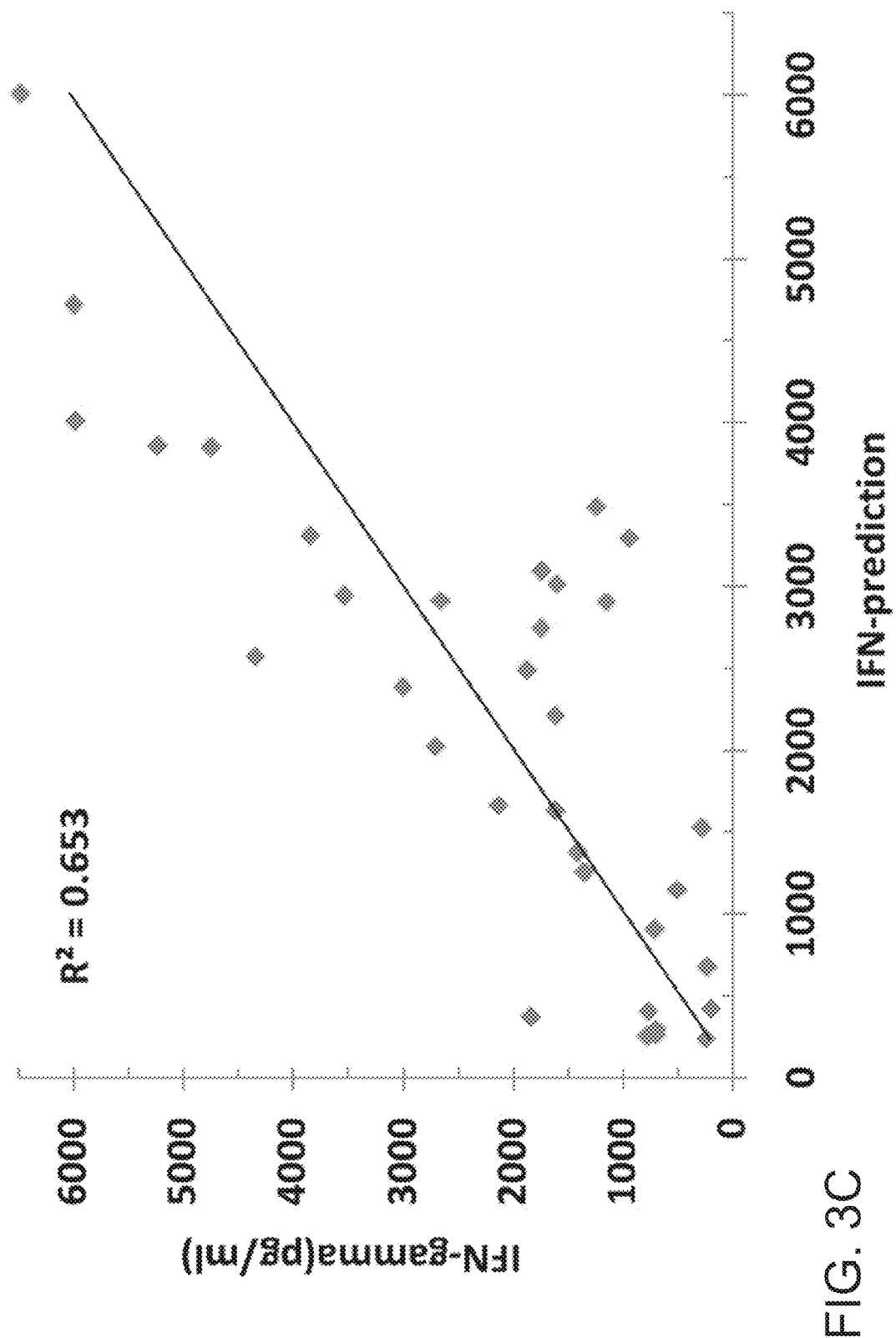

FIGS. 3A-C are plots and diagrams illustrating that TIL reactivity is largely determined by its subpopulation fractions. (A) Reactive and nonreactive TILs exhibit distinct subpopulations signatures. Columns and rows correspond to TILs and subpopulations respectively. The distance between TILs was calculated using Spearman correlation followed by hierarchical clustering. The rows were clustered similarly. The red and blue arrows represent nonreactive and reactive TILs respectively. Two main clusters emerge characterized by $CD4^+$ and $CD8^+$ overabundant subpopulations. These clusters also separate nonreactive from reactive TILs ($P<10^{-3}$). (B) A decision tree algorithm was used in order to generate a simple set of rules for classifying TIL functionality. These rules classify the TILs with 89% total accuracy. (C) Exact IFN-γ values of the reactive TILs can be described as a function of two subpopulation fractions with positive and negative weights:

$$\text{IFN-}\gamma(\text{pg/ml})=63 \cdot (CD8^+CD28^-)-50 \cdot (CD8^+CD69^+ CD33^-)+253.$$

The IFN-γ levels can be described as a balance between two opposing subpopulations with positive and negative effects and equal weights.

Figure 4B:
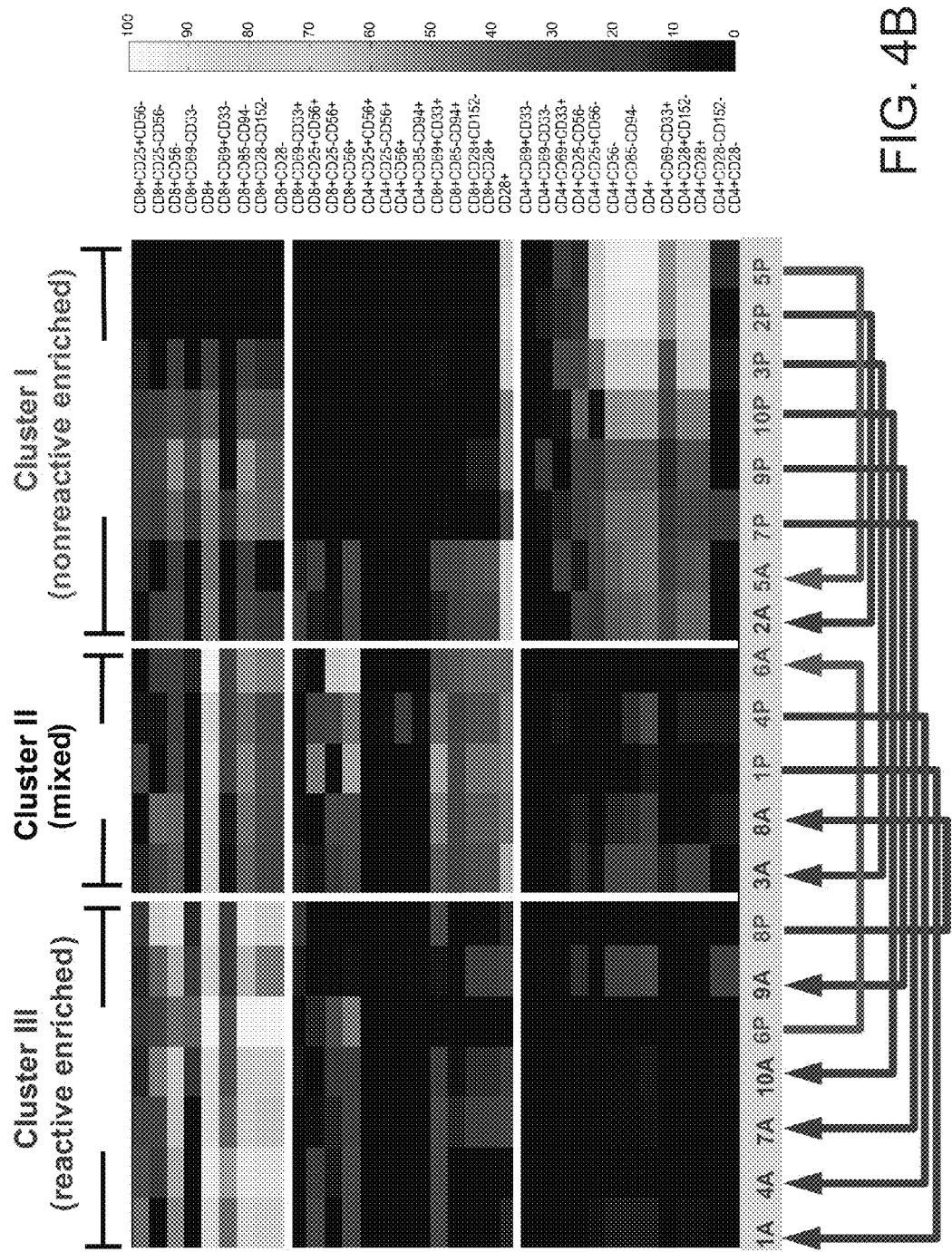
Figure 4C:
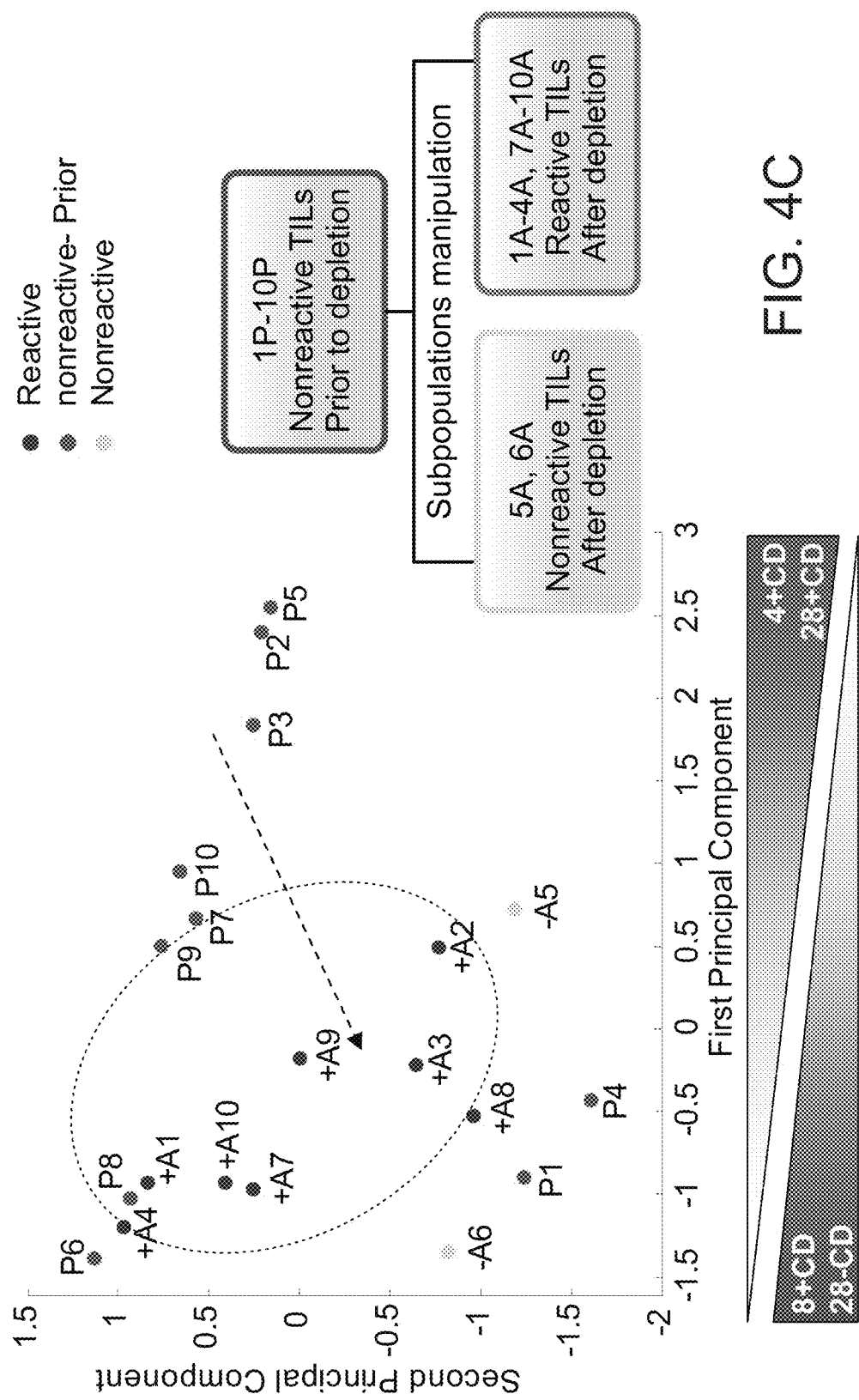

FIGS. 4A-C are graphs and diagrams showing that rational subpopulation manipulation restores TIL anti-tumor reactivity accompanied by a shift in subpopulation signature. (A) IFN-γ increases after TIL subpopulation manipulation. IFN-γ levels of 12 TILs before and after inhibitory subpopulation depletion are compared. 9 of the original nonreactive TILs show significant increase in IFN-γ. Incubation of TILs in control experiments with culture media or unrelated melanoma indicates that the increase in IFN-γ secretion does not occur spontaneously and is specific. (B) Shift in reactivity can be explained in terms of a shift in subpopulation signature prior and after depletion. The subpopulation fractions of 10 TILs prior and after subpopulation depletion were determined by flow cytometry. 8 of the original nonreactive TILs became reactive, 7 of which also showed a shift from a nonreactive subpopulation signature to a reactive one, indicated by the blue arrows. The two TILs that remained nonreactive exhibited either a minor change or a negative change in subpopulation signature as indicated by the red arrows. (C) The transformation in reactivity of a TIL can be described as a path in a two dimensional space. A simple representation of the TIL reactivity signature was obtained by applying principal component analysis (PCA) [Ian T. Jolliffe, Principal component analysis (Springer, ed. second, 2002)], which is a method for dimensionality reduction at the expense of loosing part of the data variance. The data was reduced from 35 to two dimensions. The x and y axes are principle components capturing 49% and 24% of the total variance in the data (FIGS. 11A-B). The figure shows a subspace that is overpopulated with reactive TILs. The change in reactivity can be visualized as a path from a nonreactive TIL to a TIL that resides in the reactive subspace (for example see dotted arrow).

FIGS. 5A-C are tables of the final dataset of subpopulations after the filtration procedure.

Figure 6:
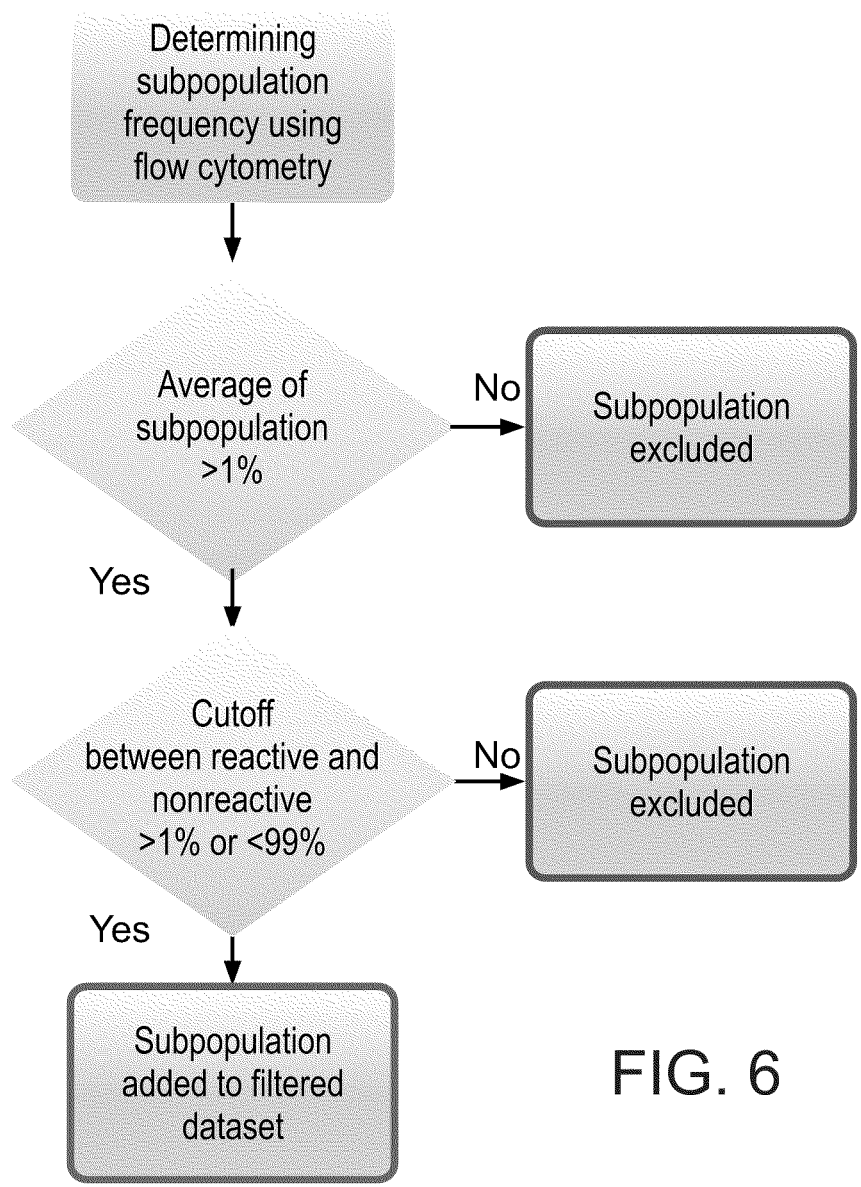

FIG. 6 is a flow chart of dataset filtering procedure.

Figure 7:
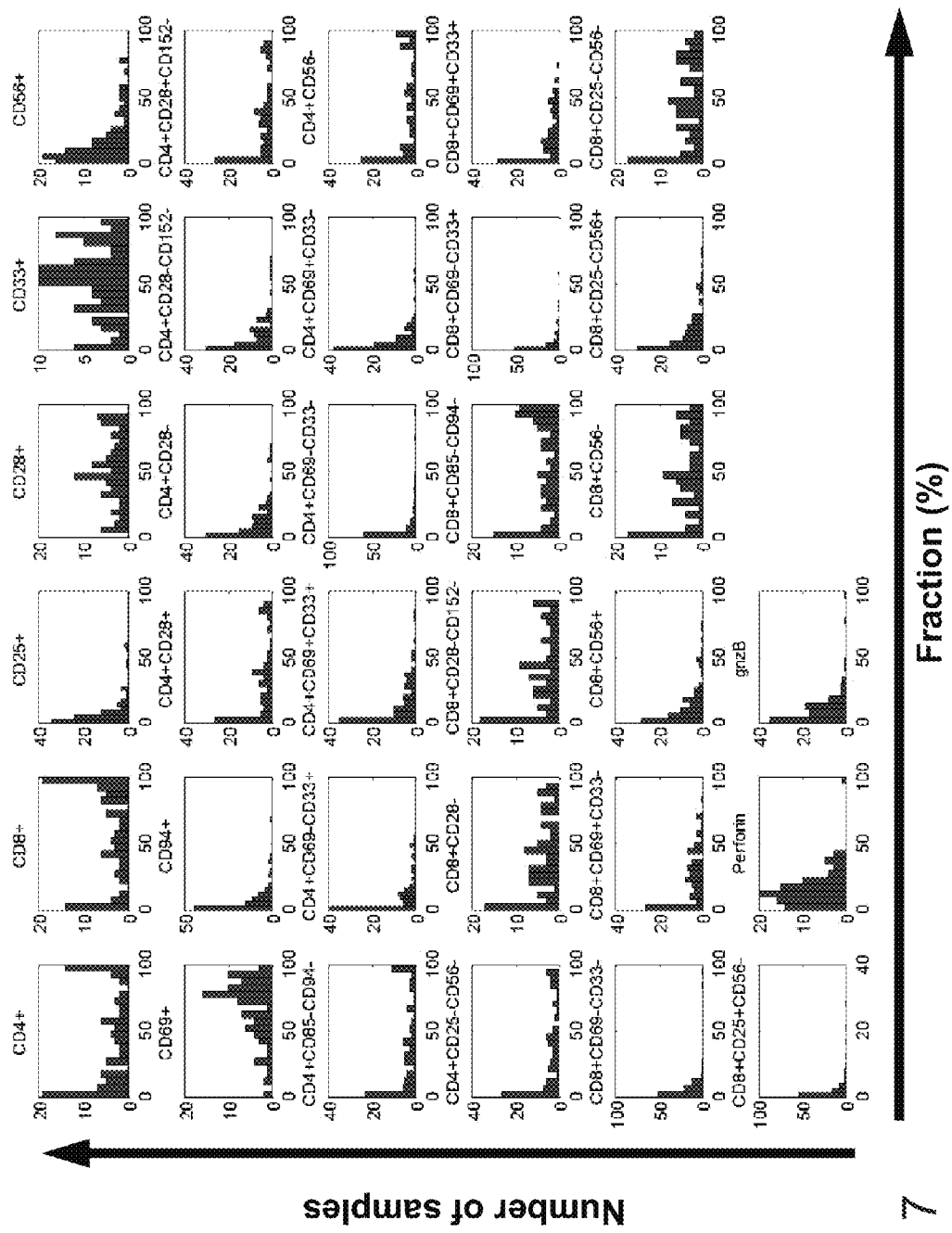

FIG. 7 are graphs illustrating the distributions of subpopulation percentages for single, double and triple staining of 91 TILs. The x-axis is subpopulation percentage and the y-axis is the number of TILs that had this percentage out of 91 TILs.

Figure 8:
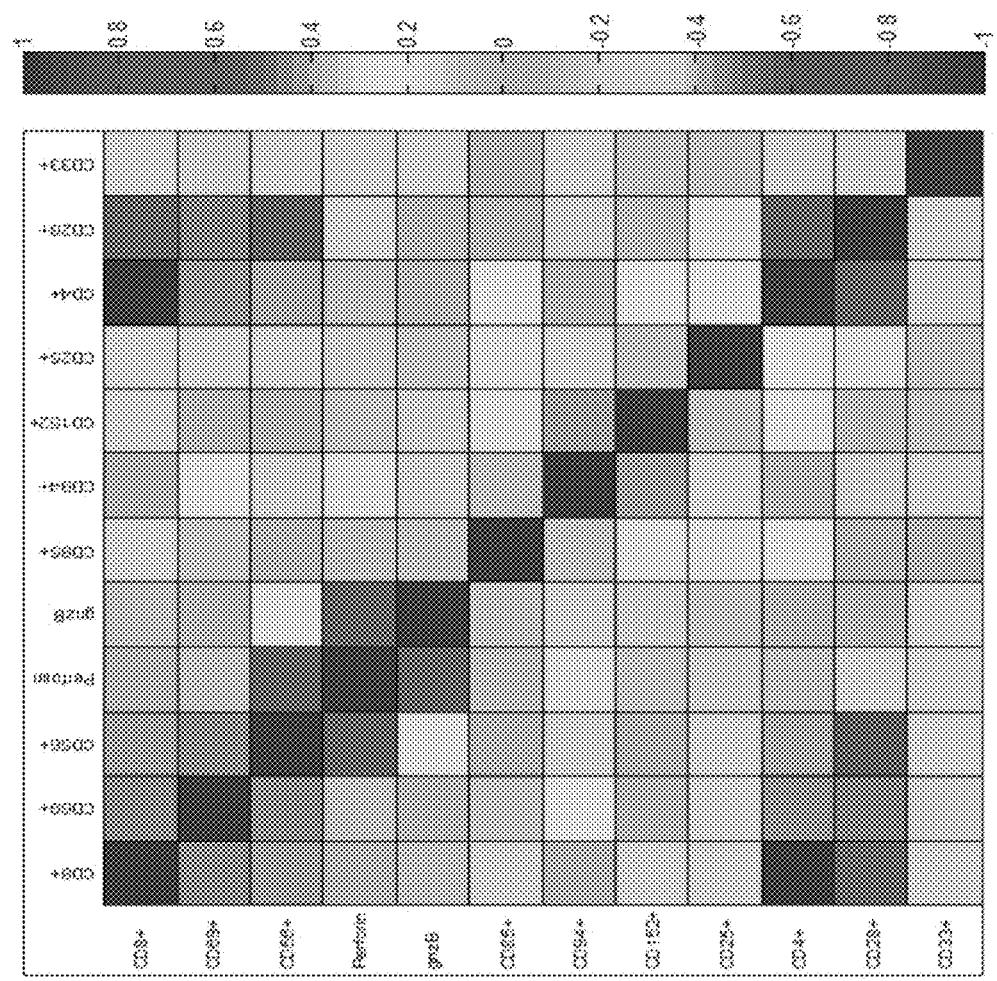

FIG. 8 is a map showing the correlation between pairs of receptors. Different groups of receptors are correlated and anti-correlated. The percentage of receptor occurrence in 91 TILs was measured using flow cytometry. Several groups of receptors show strong correlations including A: ($CD8^+$, $CD69^+$, $CD56^+$, Perforin, Grenzym); B: ($CD85^+$, $CD94^+$, $CD152^+$, $CD25^+$); and C: ($CD4^+$, $CD28^+$, $CD33^+$). Furthermore, some groups are anti-correlated, for example group A and C. The correlated receptors also share common functionality. For example group B contains three co-inhibitory receptors. This suggests that receptors with common functionality also share a common regulation at the population level.

Figure 9:
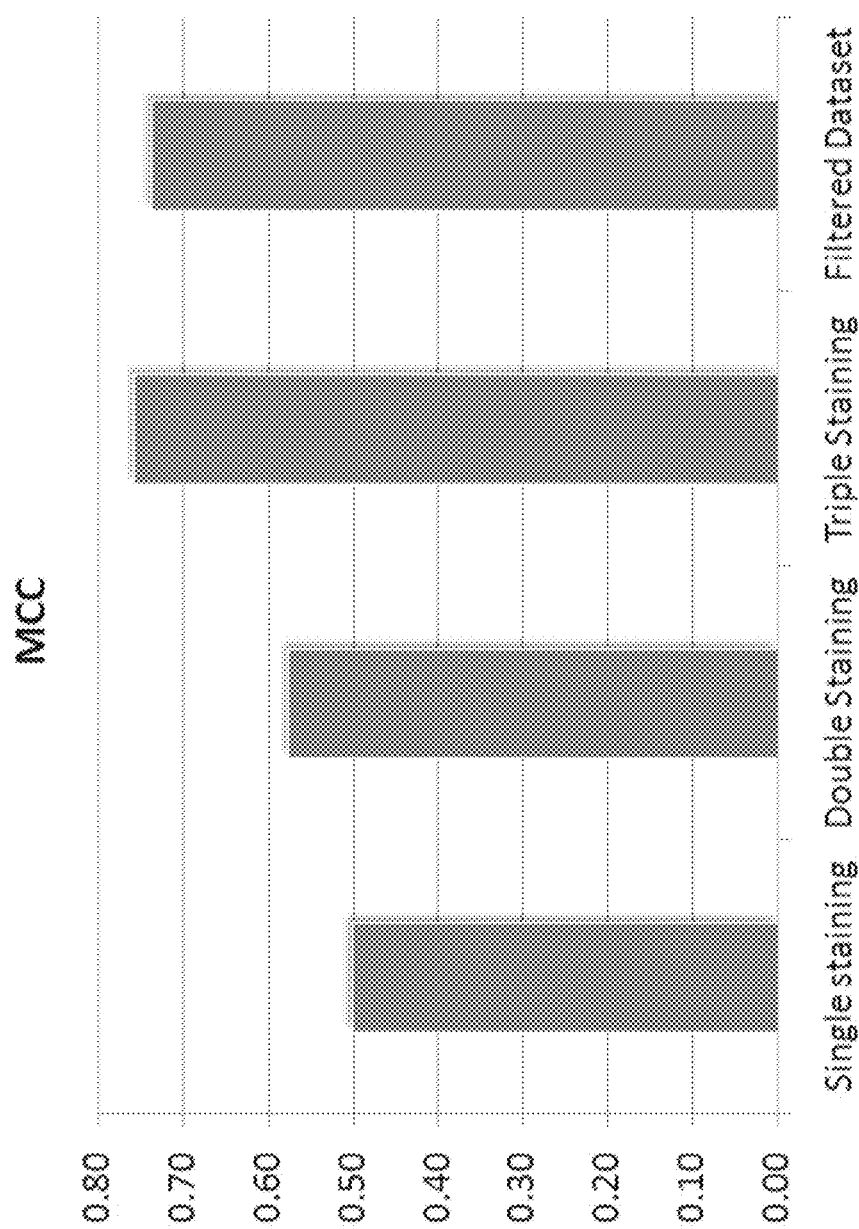

FIG. 9 is a bar graph comparing the SVM prediction accuracy between the datasets containing single, double and triple subpopulations as well as the filtered dataset.

Figure 10:
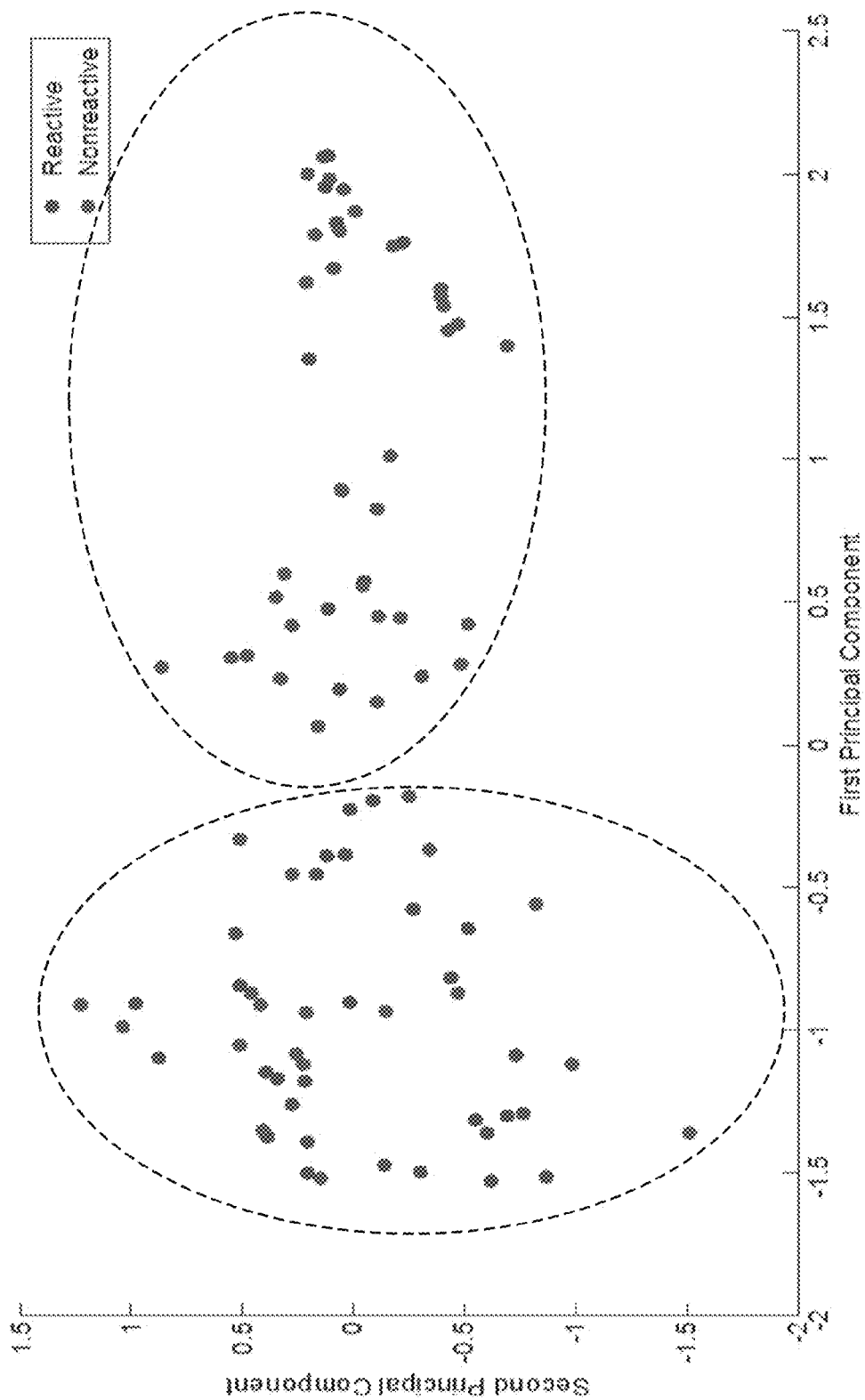

FIG. 10 is a Venn diagram illustrating that reactive TILs share a similar subpopulation signature. A simple representation of the TIL reactivity signature was obtained by applying principal component analysis (PCA). This technique enables a reduction in dimensionality at the expense of loosing some of the data variance. FIG. 10 shows a mapping from the original 33 dimensional data into two dimensions. K-means unsupervised clustering generated two distinct clusters that were enriched for reactive and nonreactive TILs (Fischer exact $P<10^{-3}$). The x and y axes explain 60% and 11% of the variance in the data respectively. Another property of TIL reactivity emerges from the subspaces in which each functional state resides. While the reactive TILs occupy a defined subspace of subpopulation combinations, as indicated by the high density of blue dots, the nonreactive TILs, indicated by red dots, are dispersed FIGS. 11A-B are bar graphs illustrating the subpopulation coefficients for the first and second principle components shown in FIG. 4C.

DESCRIPTION OF SPECIFIC EMBODIMENTS OF THE INVENTION

The present invention, in some embodiments thereof, relates to T cell populations capable of treating cancer.

Adoptive cell transfer (ACT) therapy for patients with cancer relies on the ex vivo generation of highly active tumor, specific lymphocytes, and their administration in large numbers to the autologous host.

Preclinical models have identified characteristics of lymphocyte cultures that are required for successful ACT therapy. Until presently, the most important characteristic was thought to be the presence of high affinity, tumor antigen specific $CD8^+$ cells. It was also shown that $CD4^+$ cells were also required for effective treatment of some tumors [Surman et al, J. Immunology 164, 562-565, 2000]. In contrast, it has been demonstrated that the presence of $CD4^+CD25^+$ T cells suppress autoimmunity and may be potent inhibitors of antitumor effects in mice [Shevach E. M. Nat. Rev. Immunol. 2, 389-400 (2002)]. This has led to the conclusion that lymphodepleting subpopulations comprising this signature may be beneficial for ACT therapy.

The present inventors have devised a novel method for studying the underlying composition and cellular interactions that determine the degree of TIL reactivity. This method, summarized in FIG. 1A, is based on measuring frequencies of subpopulation fractions and constructing a "subpopulations signature" for each TIL.

Using a decision tree algorithm, three subpopulations were identified as being important predictors of reactivity (FIG. 3B). These subpopulations include $CD8^+CD28^-CD152^-$, $CD94^+$ and $CD8^+CD69^+CD33^-$.

Knowledge of subpopulations that predict the reactivity of the TIL sample allowed the present inventors to control reactivity thereof. Accordingly, exploitation of this knowledge has lead to the generation of TIL populations of enhanced reactivity.

Whilst further reducing the present invention to practice, the present inventors have shown that it is possible to deplete non-reactive TILs of lymphocytes of particular subpopulation signatures and restore TIL anti-tumor reactivity (FIGS. 4A-C).

Thus, according to one aspect of the present invention, there is provided a method of determining a reactivity of a subpopulation of TILs in a TIL sample, the method comprising:

(a) assaying an activity of a statistically significant number of TIL samples;

(b) analyzing the TIL samples by flow cytometry analysis of at least three markers per cell in order to classify subpopulations of cells, wherein at least one of the three markers is CD4 or CD8, at least a second of the three markers is a cytokine or chemokine and at least a third of the three markers is an adhesion molecule, a co-inhibitory receptor, a co-stimulatory receptor or a protein set forth in Table 5; and (c) analyzing a frequency of at least one subpopulation in the TIL sample, wherein a frequency above a predetermined threshold indicates that the at least one subpopulation of cells is associated with the activity.

As used herein, the term "reactivity" refers to an ability of the TILs to at least inhibit cancer progression and optimally promote regression of same (either partially, or completely).

As used herein, the term "tumor-infiltrating lymphocytes" refers to white blood cells of a subject afflicted with a cancer (such as melanoma), that have left the blood stream and have migrated into a tumor. Thus, tumor-infiltrating lymphocytes may have tumor specificity.

Such lymphocytes can be isolated from an individual (e.g. during a tumor biopsy) to be treated by methods known in the art and cultured in vitro (Kawakami, Y. et al. (1989) J. Immunol. 142: 2453-3461). Lymphocytes may be cultured in media such as RPMI or RPMI 1640 or AIM V for 1-10 weeks. An exemplary method for obtaining TILs includes plating viable cells (e.g. $1 \times 10^6$) of a single-cell suspension of enzymatically digested explant of metastatic melanoma. It will be appreciated that the TILs may be isolated from fresh tumors or from frozen tissue (at the cost of lower yield).

The TIL samples of the present invention may be obtained from any mammalian species, such as human.

As mentioned, the method of this aspect of the present invention is effected by assaying the activities of a statistically significant number of TIL samples. It will be appreciated that the number of statistically significant TILs is dependent on the number of markers that are analyzed per cell.

Thus, typically when three marker per cell are analyzed, the statistically significant number of samples is greater than about 10. According to another embodiment, the statistically significant number of samples is greater than about 50. According to another embodiment, the statistically significant number of samples is greater than about 75. According to another embodiment, the statistically significant number of samples is greater than about 100. According to another embodiment, the statistically significant number of samples is greater than about 150. According to another embodiment, the statistically significant number of samples is greater than about 200.

Exemplary methods of assaying activities of TIL samples include $^{51}$CR release cytotoxicity assays (Cerundolo, V. et al. (1990) Nature 345:449-452) or lymphokine assays such as IFN-γ or TNF secretion assays [Schwartzentruber, D. et al., (1991) J. of Immunology 146:3674-3681].

As mentioned herein above, the method of this aspect of the present invention is further effected by analyzing the TIL samples by flow cytometry analysis of at least three markers per cell in order to classify subpopulations of cells.

As used herein, the term "flow cytometry" refers to an assay in which the proportion of a material (e.g. lymphocyte comprising a particular maker) in a sample is determined by labeling the material (e.g., by binding a labeled antibody to the material), causing a fluid stream containing the material to pass through a beam of light, separating the light emitted from the sample into constituent wavelengths by a series of filters and mirrors, and detecting the light.

A multitude of flow cytometers are commercially available including for e.g. Becton Dickinson FACScan and FACScaliber (BD Biosciences, Mountain View, Calif.). Antibodies that may be used for FACS analysis are taught in Schlossman S, Boumell L, et al, [Leucocyte Typing V. New York: Oxford University Press; 1995] and are widely commercially available.

According to one embodiment, the markers are cell surface antigens.

According to this aspect of the present invention at least one of the three markers is a cytokine or chemokine Exemplary cytokine and chemokine makers contemplated by the present invention, include, but are not limited to those set forth in Table 1.

TABLE 1

| Antigen Name | Other Names | Structure | Function |
|---|---|---|---|
| CD117 | c-kit, SCFR | IgSF, RTK family | SCF receptor, hematopoietic progenitor development/differentiation |
| CDw119 | IFNγR | | IFN-γ Rα, w/ IFN-γ AF-1, host defense |
| CD120a | TNFR-I | TNFRSF | receptor for both TNF-α and TNF-β |
| CD120b | TNFR-II | TNFRSF | receptor for both TNF-α and TNF-β |
| CD121a | IL-1R type I | IgSF | binds IL-1α and IL-1β, IL-1 signaling |
| CDw121b | IL-1R, type II | IgSF | binds IL-1α and IL-1β, negative signals |
| CD122 | IL-2Rβ | CRSF | IL-2Rβ and IL-15Rβ, signal transduction |
| CDw123 | IL-3R | CRSF | IL-3Rα, w/ CDw131 |
| CD124 | IL-4R | CRSF | IL-4Rα, w/ CD132 or IL-13Rα, T cell growth/differentiation |
| CDw125 | IL-5R | CRSF | IL-5Rα, w/ CDw131 |
| CD126 | IL-6R | IgSF, CRSF | IL-6Rα, w/ CD130 |
| CD127 | IL-7R | CRSF | IL-7Rα, w/ CD132, B and T cell development |
| CD130 | IL-6Rβ, gp130 | CRSF | IL-6Rβ, IL-6, IL-11, LIF, CNF signals |
| CDw131 | IL-3R common β | CRSF | w/ α subunits of IL-3R, IL-5R, and GM-CSFR, signal transduction |
| CD132 | Common γ | CRSF | subunit of IL-2R, IL-4R, IL-7R, IL-9R, and IL-15R, signal transduction |
| CD181 | CXCR1, IL-8RA | GPCR1 family | binding of IL-8 induces chemotaxis of neutrophils |
| CD182 | CXCR2, IL-8RB | GPCR1 family | binding of IL-8 induces chemotaxis of neutrophils |
| CD183 | CXCR3 | TM7SF | IP-10, Mig and I-TAC receptor, T cell recruitment to inflammatory sites, enhancement of Th1 response |
| CD184 | CXCR4, fusin | TM7SF | SDF-1 receptor, X4 HIV-1 coreceptor |
| CD185 | CXCR5, BLR1 | GPCR1 family | w/ chemokine BLC, possible regulatory function in Burkitt Lymphomagenesis and/or B differentiation, activation of mature B |
| CDw186 | CXCR6, BONZO | GPCR1 family | receptor for CXCL16 and coreceptor for SIV, strains of HIV-2 and m-tropic HIV-1 |
| CD191 | CCR1, MIP-1αR, RANTES-R | GPCR1 family | binds C-C type chemokines and transduces signal by increasing intracellular calcium ion levels |

TABLE 1-continued

| Antigen Name | Other Names | Structure | Function |
|---|---|---|---|
| CD192 | CCR2, MCP-1-R | GPCR1 family | binds MCP-1, MCP-3 & MCP-4, alternative coreceptor with CD4 for HIV-1 infection |
| CD193 | CCR3, CKR3 | GPCR1 family | binds eotaxin, eotaxin-3, MCP-3, MCP-4, RANTES & MIP-1δ, alternative coreceptor w/ CD4 for HIV-1 infectiongg |
| CD195 | CCR5 | | MIP-1α, MIP-1β and RANTES receptor, R5 HIV-1 coreceptor |
| CD196 | CCR6, LARC receptor, DRY6 | GPCR1 family | binds MIP-3α/LARC |
| CD197 | CCR7 | | 6Ckine and MIP-2β receptor |
| CDw198 | CCR8, GPRCY6, TER1 | GPCR1 family | allergic inflammation, alternative coreceptor with CD4 for HIV-1 infection |
| CDw199 | CCR9, GPR-9-6 | GPCR1 family | binds SCYA25/TECK, alternative coreceptor with CD4 for HIV-1 infection |
| CDw210 | IL-10-R | | IL-10 receptor, signal transduction |
| CD212 | IL-12-R β1 | | binds IL-12 w/ high affinity, associates w/ IL-12 receptor β2 |
| CD213a1 | IL-13-R α1 | | binds IL-13 w/ low affinity, w/ CD124 |
| CD213a2 | IL-13-R α2 | | binds IL-13 w/ high affinity |
| CDw217 | IL-17-R | | IL-17 receptor |
| CDw218a | IL-18Rα, IL-1Rrp | IL-1R family | binds IL-18, activation of NF-κB |
| CDw218b | IL-18Rβ, IL18RAP | IL-1R family | heterodimeric receptor with IL-18Rα to enhance IL-18 binding |
| CD234 | Duffy, DARC | | Duffy antigen chemokine receptor |
| CD25 | Tac, p55 | type I TM | IL-2Rα, w/ IL-2Rβ and γ to form high affinity complex |
| CD30 | Ki-1 | TNFRSF | CD153 receptor, lymph proliferation/apoptosis |
| CD46 | MCP | CCRSF | membrane cofactor protein, binds C3b & C4b allowing degradation by Factor I, measles virus receptor |
| CD105 | Endoglin | homodimer | cellular response to TGF-β1 |
| CD110 | MPL, TPO-R | CRSF | thrombopoietin receptor, megakaryocyte progenitor cell growth/differentiation |
| CD114 | G-CSFR | CRSF | myeloid differentiation/proliferation |
| CD115 | M-CSFR, c-fms | IgSF, RTK family | CSF-1R, monocytic differentiation/proliferation |
| CD116 | GM-CSFRα | CRSF | w/ common β, myeloid differentiation/proliferation |
| CD135 | Flt3/Flk2 | RTK family | tyrosine kinase, binds FLT3 ligand, early lymph development |
| CDw136 | MSP-R, RON | RTK family | migration, morphological change and proliferation of different target cells |
| CD140a | PDGFRα | RTK family | binds PDGF A and B |
| CD140b | PDGFRβ | RTK family | binds PDGF B |
| CD254 | TRANCE, RANKL, OPGL | TNFSF | binds OPG and RANK, osteoclast differentiation, enhances DC to stimulate naïve-T proliferation |
| CD256 | APRIL, TALL-2 | TNFSF | binds TACI & BCMA, B proliferation |
| CD257 | BLyS, BAFF, TALL-1 | TNFSF | B cell growth factor & costimulator of Ig production |
| CD258 | LIGHT, HVEM-L | TNFSF | binds LTBR, T proliferation, receptor for HVEM |
| CD261 | TRAIL-R1, DR4 | TNFRSF | contains death domain, apoptosis via FADD & caspase-8 |
| CD262 | TRAIL-R2, DR5 | TNFRSF | contains death domain, apoptosis via FADD and caspase-8 |
| CD263 | TRAIL-R3, DcR1, LIT | TNFRSF | receptor for TRAIL but lacks death domain |
| CD264 | TRAIL-R4, TRUNDD, DcR2 | TNFRSF | binds TRAIL but contains truncated death domain |
| CD265 | RANK, TRANCE-R, ODFR | TNFRSF | binds TRANCE, osteoclastogenesis, T-DC interactions |
| CD266 | TWEAK-R, FGF-inducible 14 | TNFRSF | TWEAK receptor, cell-matrix interactions and endoth growth and migration |

TABLE 1-continued

| Antigen Name | Other Names | Structure | Function |
|---|---|---|---|
| CD326 | Ep-CAM, Ly74 | TM tyr kinase | growth factor receptor? |
| CD331 | FGFR1, Fms-like tyrosine kinase-2, KAL2, N-SAM | | binds FGF, high affinity receptor for fibroblast growth factors |
| CD332 | FGFR2, BEK, KGFR | TM RTK family | binds FGF, high affinity receptor for fibroblast growth factors |
| CD333 | FGFR3, ACH, CEK2 | TM RTK family | binds FGF, high affinity receptor for fibroblast growth factors |
| CD334 | FGFR4, JTK2, TKF | TM RTK family | binds FGF, high affinity receptor for fibroblast growth factors |
| AITRL | TNFSF18, TL6, GITRL | | |
| CMKLR1 | chemokine-like receptor 1 | GPCR 7TM, chemokine receptor | binds chemerin, pDC recruitment, bone development |
| DcR3 | TR6, TNFRSF6B | Soluble | Fas decoy receptor, tumor evasion |
| HVEM | TNFRSF14, TR2 | TNFRSF | receptor for LIGHT, LT-α, BTLA, Herpes Simplex Virus, lymphocyte activation |
| IL-15Rα | | | binds to IL-15, w/ IL-2RB and common γ, IL-15 trans-presentation |
| TLR5 | TIL3 | TLR family | interacts w/ microbial lipoproteins, NF-κB, responds to Salmonella |
| TLR6 | | TLR family | interacts w/ microbial lipoproteins, protein sequence similar to hTLR1; regulates TLR2 response |
| TLR7 | | TLR family | |
| TLR8 | | TLR family | |
| TLR10 | | TLR family | most closely related to TLR1 and TLR6 |
| TSLPR | | heterodimer with IL-7Rα/CD127 | binds TSLP (Thymic Stromal Lymphopoietin) to activate DC |

According to this aspect of the present invention at least one of the three markers is an adhesion molecule, a co-inhibitory receptor, a co-stimulatory receptor or a relevant protein such as those set forth in Table 5.

Exemplary adhesion molecules contemplated by the present invention are set forth in Table 2.

TABLE 2

| Antigen Name | Other Names | Structure | Function |
|---|---|---|---|
| CD11a | LFA-1, integrin αL | Integrin family | CD11a/CD18 receptor for ICAM-1, -2, -3, intercellular adhesion, T costimulation |
| CD50 | ICAM-3 | IgSF | adhesion, costimulation |
| CD73 | | GPI-linked | ecto-5'-nucleotidase, nucleoside uptake, T costimulation, lymph adhesion |
| CD99 | MIC2, E2 | | T cell activation, adhesion |
| CD106 | VCAM-1 | IgSF | VLA-4(CD49d/CD29) receptor, leukocyte adhesion, migration, costimulation |
| CD2 | T11, LFA-2, SRBC-R | IgSF | CD58 ligand, adhesion, T cell activation |
| CD9 | p24, MRP-1 | TM4SF | cellular adhesion and migration |
| CD15 | Lewis-x, Lex | CHO | adhesion |
| CD15s | Sialyl Lewis X | CHO | CD62L and CD62P ligand, adhesion |
| CD15u | Sulfated Lewis X | CHO | adhesion |
| CD18 | Integrin β2 | Integrin family | w/ CD11a, b & c, adhesion |
| CD22 | BL-CAM, Siglec-2 | IgSF, sialoadhesins | adhesion, B-mono, B-T interactions |
| CD31 | PECAM-1 | IgSF | CD38 receptor, adhesion |
| CD33 | p67, Siglec-3 | IgSF, sialoadhesins | adhesion |

TABLE 2-continued

| Antigen Name | Other Names | Structure | Function |
|---|---|---|---|
| CD34 | | Sialomucin, type I TM | stem cell marker, adhesion, CD62L receptor |
| CD35 | CR1 | CCRSF | complement receptor 1, binds C3b and C4b, adhesion, phagocytosis |
| CD36 | GPIV | | ECM receptor, adhesion, phagocytosis |
| CD42a | GPIX | LRRF | complex w/ CD42b, c and d, receptor for vWF and thrombin, platelet adhesion to subendothelial matrices |
| CD42b | GPIbα | LRRF | complex w/ CD42a, c and d, binds to vWF and thrombin, platelet adhesion/activation |
| CD43 | Leukosialin, sialophorin | Sialomucin, type I TM | inhibition of T cell interaction, CD54R, adhesion |
| CD44 | H-CAM, Pgp-1 | hyaladherin family | binds hyaluronic acid, adhesion |
| CD44R | CD44v | | adhesion, metastasis |
| CD47 | IAP | IgSF | leukocyte adhesion, migration, activation |
| CD48 | Blast-1 | IgSF | cell adhesion |
| CD49a | VLA-1 | Integrin family | integrin α1, adhesion, CD49a/CD29 binds collagen and laminin |
| CD49b | VLA-2 | Integrin family | integrin α2, adhesion, CD49b/CD29 binds collagen and laminin |
| CD49c | VLA-3 | Integrin family | integrin α3, adhesion, CD49c/CD29 binds laminin, fibronectin and collagen |
| CD49d | VLA-4 | Integrin family | integrin α4, adhesion, CD49d/CD29 binds fibronectin, VCAM-1 & MAdCAM-1 |
| CD49e | VLA-5 | Integrin family | integrin α5, adhesion, CD49e/CD29 binds fibronectin |
| CD49f | VLA-6 | Integrin family | integrin α6, adhesion, CD49f/CD29 binds laminin |
| CD51 | Vitronectin receptor | Integrin family | integrin αv, adhesion, CD51/CD61 binds vitronectin, vWF, fibrinogen and thrombospondin |
| CD56 | NCAM | IgSF | adhesion |
| CD58 | LFA-3 | IgSF | CD2 receptor, adhesion |
| CD61 | GPIIIa | Integrin family | integrin β3, adhesion, CD41/CD61 or CD51/CD61 mediate adhesion to ECM |
| CD62P | P-selectin, PADGEM | Selectin family | CD162, CD15s receptor, adhesion, neutrophil rolling, platelet-neutrophil and platelet-mono interactions |
| CD66a | BGP-1, NCA-160 | IgSF, CEA family | cell adhesion |
| CD66b | CD67, CGM6 | IgSF, CEA family | cell adhesion, neutrophil activation |
| CD66c | NCA | IgSF, CEA family | cell adhesion |
| CD66e | CEA | IgSF, CEA family | cell adhesion |
| CD96 | TACTILE | IgSF | adhesion of activated T and NK |
| CD100 | | | cell adhesion, cellular activation |
| CD104 | β4 integrin | Integrin family | w/ integrin α6 (CD49f), cell adhesion, differentiation, metastasis |
| CD112 | PRR2, Nectin-2 | IgSF | intercellular adhesion |
| CDw113 | PVRL3, Nectin3 | IgSF | adhesion molecule that interacts with afadin |
| CD138 | Syndecan-1 | Syndecan family | receptor for ECM, cell morphology |
| CD144 | VE-Cadherin, Cadherin-5 | Cadherin family | adhesion, cell-cell interaction |
| CD146 | MUC18, S-endo | IgSF | adhesion |
| CD147 | Neurothelin, basoglin | IgSF | adhesion |
| CD151 | PETA-3 | | cell adhesion |
| CD162 | PSGL-1 | Mucin family | CD62P, CD62L ligand, adhesion, rolling |
| CD166 | ALCAM | IgSF | CD6 ligand, adhesion |
| CD167a | DDR1 | RTK family | tyrosine kinase, adhesion to collagen |
| CD168 | RHAMM | | adhesion, tumor migration, metastasis |
| CD169 | sialoadhesin, Siglec-1 | IgSF, sialoadhesins | adhesion, cell-cell and cell-matrix interactions, binds CD227 on breast cancer cells and CD43 on T cells |
| CD170 | Siglec-5, CD33-like2 | IgSF, sialoadhesins | adhesion |
| CD172a | SIRPγ | | adhesion, complex w/ CD47 |
| CD222 | IGF-II R, mannose-6 phosphate-R | Type I TM | adhesion, tumor growth, a receptor for TGFβ-LAP, plasminogen, proliferin, truncated form (220 kD) found in serum |
| CD227 | MUC1, EMA | Mucin family, type I TM | adhesion, signaling, binds CD169, CD54, & selectins |

TABLE 2-continued

| Antigen Name | Other Names | Structure | Function |
| --- | --- | --- | --- |
| CD229 | Ly-9 | IgSF | adhesion |
| CD242 | ICAM-4 | IgSF | adhesion, Landsteiner-Wiener blood group |
| CD309 | VEGFR2, KDR | Type III TM tyr kinase | binds VEGF, regulates adhesion and cell signaling |
| CD312 | EMR2 | EGFR-7TM ASV | cell adhesion and migration for phagocytosis |
| CD318 | CDCP1, SIMA135 | Type I, ASV | cell adhesion with ECM |
| CD322 | JAM2, VE-JAM | IgSF | cell adhesion, lymphocyte homing to secondary lymphoid organs |
| CD324 | E-Cadherin, Uvomorulin | cadherin SF | cell adhesion, homotypic interaction & binds αE/β7 |
| CDw325 | N-Cadherin, NCAD | cadherin SF | cell adhesion, neuronal recognition |
| CDw327 | SIGLEC6 | IgSF | adhesion, membrane-bound & secreted forms |
| CDw328 | SIGLEC7, AIRM-1 | IgSF | sialic-acid dependent adhesion, inhibit NK activation, hemopoiesis |
| CDw329 | SIGLEC9 | IgSF | sialic-acid dependent adhesion molecule |
| CD11b | Mac-1, integrin αM | Integrin family | binds CD54, ECM, iC3b |
| CD11c | p150, 95, CR4, integrin αX | Integrin family | binds CD54, fibrinogen and iC3b |
| CD24 | BA-1 | GPI-linked | binds P-selectin |
| CD29 | Integrin β1 | Integrin family | w/ CD49a (VLA-1) receptor for VCAM-1, MAdCAM-1 and ECM |
| CD41 | gpIIb | Integrin family | w/ CD61 forms GPIIb, binds fibrinogen, fibronectin, vWF, thrombospondin, platelet activation and aggregation |
| CD42c | GPIbb | LRRF | complex w/ CD42a, b, d |
| CD42d | GPV | LRRF | complex w/ CD42a-c |
| CD54 | ICAM-1 | IgSF | receptor for CD11a/CD18 (LFA-1), CD11b/CD18 (Mac-1) and rhinovirus |
| CD62E | E-selectin, ELAM-1 | Selectin family | binds CD15s, cell rolling, metastasis |
| CD62L | L-selectin, LECAM-1 | Selectin family | CD34, GlyCAM, and MAdCAM-1 receptor, leukocyte homing, tethering, rolling |
| CD66d | CGM1 | IgSF, CEA family | |
| CD66f | PSG, Sp-1 | IgSF, CEA family | immune regulation, protects fetus from maternal immune system |
| CD69 | AIM | C-type lectin | signal transduction |
| CD75 | | CHO Sialoglycan family | lactosamines |
| CD75s | | CHO Sialoglycan family | α-2,6-sialylated lactosamines (previously CDw75 and CDw76) |
| CD103 | HML-1, α6, integrin αE | Integrin family | w/ integrin β7, binds E-cadherin, lymph homing/retention |
| CD111 | PRR1, Nectin-1 | IgSF | |
| CD133 | AC133, prominin-like 1 | TM5SF | |
| CD141 | Thrombomodulin | C-type lectin | initiation of protein C anticoagulant signal |
| CD156a | ADAM8 | | leukocyte extravasation |
| CD280 | ENDO180, UPARAP | C-type lectin SF | mannose receptor, collagen matrix remodeling and endocytic recycling |
| CD303 | BDCA2, HECL | C-type lectin SF ASV | inhibit IFN-α production |
| CD321 | JAM1, F11 receptor | IgSF, Type I, ASV | tight junctions |
| Integrin β5 | | | w/ αv subunit, vitronectin receptor |

Exemplary co-stimulatory receptors contemplated by the present invention are set forth in Table 3.

TABLE 3

| Antigen Name | Other Names | Structure | Function |
|---|---|---|---|
| CD6 | T12 | Scavenger R SF | CD166 receptor, T cell differentiation/costimulation |
| CD7 | | IgSF | T costimulation |
| CD26 | DPP IV | type II TM | dipeptidyl peptidase, T costimulation, HIV entry |
| CD27 | T14 | TNFRSF | CD70 receptor, T costimulation |
| CD28 | Tp44, T44 | IgSF | CD80, CD86 receptor, T costimulation |
| CD40 | | TNFRSF | CD154 receptor, B differentiation/costimulation, isotype-switching, rescues B cells from apoptosis |
| CD60a | GD3 | CHO | costimulation |
| CD70 | Ki-24 | TNFSF | CD27 ligand, T and B cell costimulation |
| CD80 | B7, B7-1, BB1 | IgSF | binds to CD28, CD152, T costimulation |
| CD81 | TAPA-1 | TM4SF | complex w/ CD19 & CD21, signaling, T costimulation |
| CD86 | B70, B7-2 | IgSF | binds to CD28, CD152, T costimulation |
| CD102 | ICAM-2 | IgSF | binds CD11a/CD18, costimulation |
| CDw137 | 4-1BB | TNFRSF | T costimulation |
| CD150 | SLAM | IgSF | costimulation, proliferation, Ig production, measles virus receptor |
| CD152 | CTLA-4 | IgSF | CD80 and CD86 receptor, negative regulation of T cell costimulation |
| CD153 | CD30L | TNFSF | CD30 ligand, T costimulation |
| CD154 | CD40L, gp39, TRAP | TNFSF | CD40 ligand, B and DC costimulation |
| CD160 | BY55 | IgSF | costimulation |
| CD171 | L1 | IgSF | kidney morphogenesis, lymph node architecture, T costimulation, neurohistogenesis, homotypic interaction, binds CD9, CD24, CD56, CD142, CD166, integrins |
| CD252 | OX-40Ligand, gp34 | TNFSF | T costimulation |
| CD273 | B7DC, PD-L2, PDCD1L2 | IgSF | PD-1 receptor, costimulation or suppression of T proliferation |
| CD274 | B7-H1, PD-L1 | IgSF | PD-1 receptor, costimulation of lymphocytes |
| CD275 | B7-H2, ICOSL, B7-RP1, GL50 | B7 Family | costimulation, cytokine production |
| CD276 | B7-H3 | B7 Family, ASV | costimulation, T activation |
| CD278 | ICOS, AILIM | CD28 family | binds ICOS-L, T costimulation |
| CD314 | NKG2D, KLR | Type II lectin-like receptor | binds MHC class I, MICA, MICB, Rae1 & ULBP4, activates cytolysis and cytokine production, costimulation |
| CD38 | T10 | | ecto-ADP-ribosyl cyclase, cell activation |
| CD45 | LCA, T200, B220 | | tyrosine phosphatase, enhanced TCR & BCR signals |
| CD45RA | | | exon A isoforms of CD45 |
| CD45RB | | | exon B isoforms of CD45 |
| CD45RO | | | isoform of CD45 lacking A, B, C exons |
| CD63 | LIMP, LAMP-3 | TM4SF | lysosomal membrane protein, moves to cell surface after activation |
| CD83 | HB15 | IgSF | |
| CD101 | V7, p126 | IgSF | T cell activation |
| CD134 | OX-40 | TNFRSF | T cell activation, differentiation, apoptosis |
| CD148 | HPTP-eta | | tyrosine phosphatase R Type III |
| CD161 | NKR-P1A | C-type lectin | NK cell-mediated cytotoxicity |
| CD221 | IGF-1 R | | binds IGF w/ high affinity, signaling, cell proliferation/differentiation |
| CD243 | MDR-1, p170, P-gp | | ion pump |
| CD244 | 2B4 | type II TM | NK activation, CD48 ligand |
| CD247 | TCRz | RTK family | TCR complex subunit, coupling of antigen recognition to signaling |
| CD277 | BT3.1, butyrophilin SF3 A1, BTF5 | B7/BT family, ASV | T activation |

TABLE 3-continued

| Antigen Name | Other Names | Structure | Function |
|---|---|---|---|
| CD319 | CRACC, SLAMF7 | Ig TM | regulate T and NK cells |
| CD335 | NKp46, Ly-94 homolog | IgSF | activates NK cells upon non-MHC ligand binding |
| CD336 | NKp44, Ly-95 homolog | IgSF | activates NK cells upon non-MHC ligand binding |
| CD337 | NKp30, Ly117 | IgSF | activates NK cells upon non-MHC ligand binding |
| 4-1BB Ligand | CD137L | TNFSF | T costimulation |
| AITR | TNFRSF18, GITR | | costimulation |
| SLP-76 | | | T cell receptor mediated signaling |
| T-bet | | | transcription factor, T development/differentiation |
| TCR αβ | | | antigen recognition |
| TCR γδ | | | antigen recognition |

Exemplary co-inhibitory receptor markers contemplated by the present invention are set forth in Table 4.

TABLE 4

| Antigen Name | Other Names | Structure | Function |
|---|---|---|---|
| CD158a | p58.1 | IgSF, KIR family | inhibition of NK cell cytolytic activity, MHC class-I specific NK receptor |
| CD158b | p58.2 | IgSF, KIR family | inhibition of NK cell cytolytic activity, MHC class-I specific NK receptor |
| CD85 | | IgSF, ILT/LIR family | inhibition of NK, T cell cytolytic function |
| CD200 | OX-2 | | inhibition of immune response |
| CD272 | BTLA | IgSF | HVEM receptor, inhibitory response |
| CD294 | CRTH2, GPR44 | GPCR-7TM | binds prostaglandin D2, stimulatory effects on Th2, allergic inflammation |
| CD305 | LAIR1 | IgSF, ASV | inhibitory receptor on NK and T cells |
| CD77 | Gb3, Pk blood group | | apoptosis |
| CD94 | KP43 | C-type lectin | complex w/ NKG2, inhibits NK function |
| CD118 | LIFR, gp190 | Type I CRSF & secreted forms | membrane-bound involved in signal transduction, soluble form inhibits activity of LIF |
| CD159c | NKG2C | Type II C-Type Lectin | w/ MHC class I HLA-E molecules, forms heterodimer with CD94 |
| CD253 | TRAIL, Apo-2L, TL2, TNFSF10 | TNFSF | death |
| CD279 | PD1, SLEB2 | | B7-H1 & B7-DC receptor, autoimmune disease and peripheral tolerance |
| CD300c | CMRF35A, LIR | IgSF | unknown |
| B7-H4 | B7-S1, B7x | B7 family | may interact with BTLA (?), inhibition |
| BAMBI | TGFBR | TGFBR | pseudoreceptor for TGF-β (short cytoplasmic domain), growth inhibition |
| DR6 | TR7 | TNFRSF | death, Th2 response |
| Foxp3 | SCURFIN | Fox family forkhead | transcription factor, upregulated in T regs |
| TWEAK | TNFSF12, APO3L | TNFSF | death |

Other markers contemplated by the present invention include those set forth in Table 5 herein below.

TABLE 5

| Antigen Name | Other Names | Structure | Function |
|---|---|---|---|
| CD88 | C5aR | TM7SF | C5a receptor, granulocyte activation |
| CD89 | FcαR | IgSF | IgA receptor, phagocytosis, degranulation, respiratory burst |
| CD5 | T1, Tp67 | Scavenger R SF | CD72 receptor, TCR or BCR signaling, T-B interaction |
| CD159a | NKG2A | | w/ CD94, NK cell receptor |
| CD163 | 130 kD | Scavenger receptor SF | |
| CD173 | Blood group H type 2 | CHO | |
| CD174 | Lewis Y | CHO | |
| CD175 | Tn | CHO | |
| CD175s | Sialyl-Tn | CHO | |
| CD176 | Thomson Friedrenreich Ag | CHO | |
| CD177 | NB1 | | |
| CD178 | FasL, CD95L | TNFSF | CD95 ligand, apoptosis, immune privilege, soluble form in serum |
| CD2R | T11-3 | IgSF | activation-dependent form of CD2 |
| CD3γ, CD3δ | T3 | IgSF | w/ TCR, TCR surface expression/signal transduction |
| CD3ε | T3 | IgSF | w/ TCR, TCR surface expression/signal transduction |
| CD4 | T4 | IgSF | MHC class II coreceptor, HIV receptor, T cell differentiation/activation |
| CD8a | T8, Leu-2 | IgSF | MHC class I coreceptor, receptor for some mutated HIV-1, T cell differentiation/activation |
| CD8b | | IgSF | |
| CD14 | LPS-R | GPI-linked | receptor for LPS/LBP, LPS recognition |
| CD16a | FcγRIIIA | IgSF | component of low affinity Fc receptor, phagocytosis and ADCC |
| CD16b | FcγRIIIB | IgSF | component of low affinity Fc receptor, phagocytosis and ADCC |
| CD23 | FcεRII | C-type lectin | CD19-CD21-CD81 receptor, IgE low affinity receptor, signal transduction |
| CD32 | FcγRII | IgSF | low affinity Fc receptor for aggregated Ig and immune complexes |
| CD39 | | NK, mac, Langerhans cells, DC, Bact | |
| CD55 | DAF | GPI-linked | binds C3b, complement regulation |
| CD57 | HNK-1, Leu-7 | | |
| CD64 | FcγRI | IgSF | high affinity receptor for IgG, phagocytosis and ADCC |
| CD71 | T9 | | transferrin receptor, iron uptake |
| CD74 | Ii, invariant chain | | MHC class II traffic and function |
| CD87 | UPA-R | GPI-linked | urokinase plasminogen activator receptor, inflammatory cell invasion, metastasis |
| CD91 | | LDLR family | receptor for α-2-macroglobulin |
| CD95 | Apo-1, Fas | TNFRSF | FasL (CD178) receptor, apoptosis |
| CD107a | LAMP-1 | | a lysosomal membrane protein |
| CD107b | LAMP-2 | | a lysosomal membrane protein |
| CD156b | TACE/ADAM 17 | | cleaves membrane proteins (TNF, TGFα) to generate soluble forms |
| CDw156c | ADAM10 | Peptidase M12B family | proteolytic cleavage of cell-surface molecules including Notch, TNF-α, APP and ephrin-A2 |
| CD165 | AD2, gp37 | lymph subset, mono, immature thymocytes, platelets | |
| CD281 | TLR1 | TLR family | innate immunity, w/ TLR2 |
| CD282 | TLR2 | TLR family | binds dsRNA, response to bacterial lipoproteins, innate immunity |
| CD283 | TLR3 | TLR family, ASV | binds dsRNA, innate immunity |

TABLE 5-continued

| Antigen Name | Other Names | Structure | Function |
|---|---|---|---|
| CD284 | TLR4 | TLR family, ASV | binds LPS, innate immunity |
| CD289 | TLR9 | TLR family | binds CpG-DNA, innate immunity |
| CDw338 | ABCG2, BCRP, Bcrp1, MXR | GPCR 7TM | multi-drug resistance transporter |
| FcεRIα | high-affinity IgE receptor | tetramer complex | triggers IgE-mediated allergic reactions |
| Granzyme B | Granzyme-2, CTLA-1 | Peptidase S1 family | target cell apoptotic lysis, cell-mediated immune responses |
| HLA-ABC | | | cell-mediated immune response & tumor surveillance |
| HLA-DR | | | presentation of peptides to CD4+ T lymphocytes |
| MICA/MICB | | MHC Class I-related proteins | unregulated on epith after shock, NKG2D receptors |
| p38 | | SAP/MAP kinase | role in cytolytic activity |
| Perforin | | | cytolytic protein |
| Stro-1 | | | surface marker for immature mesenchymal cells |

Following flow cytometry analysis, each TIL sample can be classified into subpopulations as described in the Examples section below. By measuring the frequency of each subpopulation in an already defined reactive/non-reactive sample, the significance of the subpopulation may be effected. Thus subpopulations above a predetermined threshold in a reactive TIL sample may be classified as positive predictors. Conversely, subpopulations above a predetermined threshold in a non-reactive TIL sample may be classified as negative predictors.

The predetermined thresholds may be determined using mathematical algorithms as exemplified in the FIG. 3B of the Examples section below.

According to an embodiment of this aspect of the present invention, only subpopulations above a frequency of about 1% are considered significant.

As explained in the Examples section below, the present inventors utilized this method to screen a significantly relevant number of TILs (91) and incorporated all the information gleaned into a diagrammatic representation of reactive marker signatures (FIG. 3A). Such marker signatures may be used to predict T cell responsiveness to a cancer in a subject.

Thus, according to another aspect of the present invention, there is provided a method of predicting T cell responsiveness to a cancer in a subject, comprising analyzing subpopulation marker signatures in a TIL sample of the subject, wherein a subpopulation marker signature corresponding to a reactive marker signatures as defined by FIG. 3A is indicative of T cell responsiveness and a subpopulation marker signature corresponding to a non-reactive marker signature as defined by FIG. 3A is indicative of a non T cell responsiveness.

As used herein, the term "signature" refers to an expression pattern of the indicated markers.

According to this aspect of the present invention the cancer to which T cell responsiveness is predicted includes melanoma, lung carcinoma, breast cancer, colon cancer, prostate cancer, ovarian carcinoma, renal cell carcinoma, glioma and the like. The cancer may be metastatic or non-metastatic.

As used herein, the term "melanoma" refers to metastatic melanomas, melanomas derived from either melanocytes or melanocytes related nevus cells, melanocarcinomas, melanoepitheliomas, melanosarcomas, melanoma in situ, superficial spreading melanoma, nodular melanoma, lentigo maligna melanoma, acral lentiginous melanoma, invasive melanoma or familial atypical mole and melanoma (FAM-M) syndrome. Such melanomas in mammals may be caused by, chromosomal abnormalities, degenerative growth and developmental disorders, mitogenic agents, ultraviolet radiation (UV), viral infections, inappropriate tissue expression of a gene, alterations in expression of a gene, or carcinogenic agents.

By determining reactivity of subpopulations of TILs in TIL samples, the present inventors identified three subpopulations as being important predictors of reactivity. These subpopulations include $CD8^+CD28^-CD152^-$, $CD94^+$ and $CD8^+CD69^+CD33^-$.

Thus according to yet another aspect of the present invention, there is provided a method of determining responsiveness to cancer treatment in a subject in need thereof, the method comprising analyzing a frequency of tumor infiltrating lymphocytes (TILs) having a $CD8^+CD28^-CD152^-$ signature in a sample of the subject, wherein a frequency of TILs having the $CD8^+CD28^-CD152^-$ signature above a predetermined level is indicative of a positive responsiveness to cancer treatment.

According to this aspect of the present invention, the cancer treatment is any treatment which involves the use of TILs, such as for example adoptive transfer therapy.

According to this aspect of the present invention, the number of TILs in a TIL sample having a $CD8^+CD28^-CD152^-$ signature is greater than 25%, more preferably greater than 35% and even more preferably greater than 45%.

The present inventors have shown that a TIL sample comprising a significant percentage of $CD8^+CD69^+CD33^-$ bearing lymphocytes which already comprises a significant percentage of $CD8^+CD28^-CD152^-$ bearing lymphocytes is indicative of a negative responsiveness to cancer.

According to this embodiment, the predetermined level of $CD8^+CD69^+CD33^-$ bearing lymphocytes is typically greater than about 40%, more preferably greater than about 50% and even more preferably greater than about 60%.

According to still another aspect of the present invention, there is provided a method of determining responsiveness to cancer treatment in a subject in need thereof, the method comprising analyzing a frequency of tumor infiltrating lymphocytes (TILs) having a CD8⁺CD28⁻CD152⁻ signature in a sample of the subject, wherein a frequency of TILs having the CD8⁺CD28⁻CD152⁻ signature below a predetermined level is indicative of a negative responsiveness to cancer treatment.

According to this aspect of the present invention, the number of TILs having a CD8⁺CD28⁻CD152⁻ signature is less than about 25%, more preferably less than about 35% and even more preferably less than about 45%.

The present inventors have shown that a TIL sample comprising a significant percentage of CD94⁺ bearing lymphocytes which already comprises a significantly low percentage of CD8⁺CD28⁻CD152⁻ bearing lymphocytes is further indicative of a negative responsiveness to cancer.

According to this embodiment, the predetermined level of CD94⁺ bearing lymphocytes is typically greater than about 0.5%, more preferably greater than about 0.6% and even more preferably greater than about 0.7%.

Other T lymphocyte signatures which have been shown to be predictors of effective cancer treatment include CD56+, CD4+CD85−CD94−, CD8+CD33+CD69+ and CD4+CD33−CD69+. Thus for example, when more than about 20% of the TILs in a sample comprise a CD56+ signature, this is indicative of a TIL sample being effective for cancer treatment. When more than about 38% of the TILs in a sample comprise a CD4+CD85−CD94− signature, this is indicative of a TIL sample being non-effective for cancer treatment. When more than about 17% of the TILs in a sample comprise a CD8+CD33+CD69+ signature, this is indicative of a TIL sample being effective for cancer treatment. When more than about 10% of the TILs in a sample comprise a CD4+CD33−CD69+ signature, this is indicative of a TIL sample being non-effective for cancer treatment.

By determining reactivity of subpopulations of TILs in a TIL sample, the present inventors uncovered several markers which predicted a negative responsiveness to cancer treatment. Thus, by depleting a TIL sample of those TILs which express the markers associated with negative responsiveness (i.e., lack of responsiveness), also referred to herein as "harmful markers" the present inventors postulated they should be able to increase the reactivity of the TIL sample. As shown in FIGS. 4A-C a TIL sample depleted of lymphocytes bearing a CD4, CD152, CD28, CD85 and/or CD94 marker comprised an increased reactivity towards autologous cancer cells.

Thus, according to still another aspect of the present invention, there is provided a method of treating cancer in a subject in need thereof, the method comprising depleting lymphocytes from a sample of TILs of the subject, wherein the lymphocytes express CD4, CD152 and/or CD28.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein, the phrase "subject in need thereof" refers to a subject which has the disease. The subject may be a mammal, e.g. a human. For example if the disease being treated is melanoma, the subject is typically one being diagnosed with melanoma, with or without metastasis, at any stage of the disease (e.g. IA, IB, IIA, IIB, IIC, IIIA, IIIB, IIIC or IV).

The term "depleting" as used herein refers to a procedure that substantially removes the indicated T lymphocyte population from the TIL sample without also substantially removing the "effective" lymphocytes from the composition—i.e. those capable of destroying the tumor—e.g. the subpopulation having a CD8⁺CD28⁻CD152⁻ signature.

The term "substantially removes" with respect to depletion of each of the cell types is intended to mean removal of at least 50% or more of the particular cell type, such as at least about 75%, about 80%, about 90%, about 95%, or about 97%, including at least 99%, 99.5%, 99.9% or more of the particular cell type.

Thus, by depleting lymphocytes express CD4, CD152 and/or CD28 from a TIL sample, the remaining cells are substantially enriched for T lymphocytes comprising an "effective" lymphocyte population such as those comprising a CD8⁺CD28⁻CD152⁻ signature.

According to one embodiment, depleting lymphocytes expressing the above mentioned markers may be effected by affinity labeling followed by label based separation. Thus, a fluorescently labeled anti-CD4, anti-CD152 or anti-CD28 antibody which specifically binds the "harmful" T-lymphocyte subpopulation (i.e. those T lymphocytes which deter the "effective" T lymphocytes from destroying a tumor) may be used to separate the "harmful" T lymphocytes from the "effective" T lymphocytes.

According to still further features in the described preferred embodiments, depletion of T-lymphocytes expressing the above mentioned markers may be effected by affinity purification.

For example, a substrate including an antibody or a ligand capable of specifically binding CD4, CD152 and/or CD28, can be used to effectively deplete the "harmful" T-lymphocytes from the TIL sample.

The affinity substrate according to the present invention can be a column matrix such as, for example agarose, cellulose and the like, or beads such as, for example, magnetic beads onto which the antibodies described above, are immobilized.

Thus, according to this aspect of the present invention, depletion of T-lymphocytes expressing CD4, CD152 and/or CD28, can be effected via column chromatography or magnetic bead separation.

It will be appreciated that the TIL sample may be depleted of other subpopulations of T lymphocytes including for example those that express CD85 and/or CD94.

As mentioned above, depletion of "harmful" T lymphocyte populations from the TIL sample effectively enriches for a T lymphocyte population which is effective at destroying the tumor.

Thus, according to another aspect of this invention, there is provided a method of treating cancer in a subject in need thereof, the method comprising enriching for a subpopulation of lymphocytes from a sample of TILs of the subject, the subpopulation expressing a CD8⁺CD28⁻CD152⁻ signature.

As used herein, the term "enriching" refers to a procedure which allows the TIL composition to comprise at least about 50%, preferably at least about 70%, more preferably at least about 80%, about 95%, about 97%, about 99% or more T lymphocytes comprising the CD8⁺CD28⁻CD152⁻ signature.

The enriching may be effected using known cell sorting procedures such as by using a fluorescence-activated cell sorter (FACS).

It will be appreciated that the enriching may also be effected by depleting of non-relevant subpopulations as further described herein above.

The TIL population may also be enriched for other subpopulations (e.g. a subpopulation that expresses a CD4+CD33−CD69+ signature) in order to further enhance reactivity against tumors.

Following enrichment of a TIL sample for a particular subpopulation of lymphocytes (or depletion of a TIL sample of a particular subpopulation of lymphocytes e.g. CD8⁺

CD69+CD33− or CD69+), the lymphocytes are typically expanded ex-vivo and re-injected back into the patient following leuko-depletion.

Expansion of T-cell cultures can be accomplished by any of a number of methods as are known in the arts. For example, T cells may be expanded utilizing non-specific T-cell receptor stimulation in the presence of feeder lymphocytes and either IL-2 or IL-15. The non-specific T-cell receptor stimulus can consist of around 30 ng/ml of OKT3, a mouse monoclonal anti-CD3 antibody available from Ortho, Raritan, N.J.

The autologous T-cells may be modified to express a T-cell growth factor that promotes the growth and activation thereof. Any suitable methods of modification may be used. See, e.g., Sambrook and Russell, Molecular Cloning, $3^{rd}$ ed., SCHL Press (2001). Desirably, modified autologous T-cells express the T-cell growth factor at high levels. T-cell growth factor coding sequences, such as that of IL-2, are readily available in the art, as are promoters, the operable linkage of which to a T-cell growth factor coding sequence promote high-level expression.

The T-cells can be administered by any suitable route as known in the art. For example, the T-cells may be administered as an intra-arterial or intravenous infusion, which preferably lasts approximately 30-60 minutes. Other examples of routes of administration include intraperitoneal, intrathecal and intralymphatic.

A suitable dose of T-cells to be administered is from about $2.3 \times 10^{10}$ T-cells to about $13.7 \times 10^{10}$ T-cells.

According to one embodiment, the T cells are administered to the subject together with a T-cell growth factor. The T-cell growth factor can be any suitable growth factor that promotes the growth and activation of the autologous T-cells administered. Examples of suitable T-cell growth factors include IL-2, IL-7 and IL-15, which can be used alone or in various combinations, such as IL-2 and IL-7, IL-2 and IL-15, IL-7 and IL-15, or IL-2, IL-7 and IL-15. IL-2 is available from Chiron, Emerwlle, Calif., whereas IL-7 is available from Cytheris, Vanves, Frances. IL-15 can be obtained from PeproTech, Inc., Rocky Hill, N.J.

The T-cell growth factor can be administered by any suitable route. If more than one T-cell growth factor is administered, they can be administered simultaneously or sequentially, in any order, and by the same route or different routes. According to one embodiment, the T-cell growth factor, such as IL-2, is administered intravenously as a bolus injection. A typical dosage of IL-2 is about 720,000 IU/kg, administered three times daily until tolerance.

The nonmyeloablative lymphodepleting chemotherapy can be any suitable such therapy, which can be administered by any suitable route. The nonmyeloablative lymphodepleting chemotherapy can comprise the administration of cyclophosphamide and fludarabine, particularly if the cancer is melanoma. A preferred route of administering cyclophosphamide and fludarabine is intravenously. Likewise, any suitable dose of cyclophosphamide and fludarabine can be administered. For melanom, typically around 60 mg/kg of cyclophosphamide are administered for two days after which around 25 mg/m² fludarabine are administered for five days.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

Examples

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8$^{th}$ Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Determination of Immune Subpopulation Composition of IFN-γ Secreting TILs (Tumor Infiltrating Lymphocytes)

Materials and Methods

Measurement of IFN-γ Secretion:

IFN-γ secretion was measured after co-incubation of $10^5$ TIL cells with $10^5$ viable autologous melanoma cells for an overnight period. The amount of IFN-γ secretion in the culture supernatant was detected using standard sandwich ELISA protocol.

Flow Cytometry:

The markers used for subpopulation mapping included combinations of triple staining from the pool of the following surface receptors: CD3, CD4, CD8, CD25, CD28, CD33, CD56, CD69, CD85, CD94, CD152 (FIG. 1B) and the intracellular cytotoxic proteins perforin and granzyme B.

The following antibodies (Abs) were purchased from DakoCytomation: CD4, CD25, CD28, CD56, CD69, CD85, CD94, CD152. The following Abs were purchased from BD Pharmingen: CD3, CD8, CD33. Perforin and Granzyme B antibodies were purchased from eBioscience.

For flow cytometric analysis of cell surface, $2.5 \times 10^5$ cells were washed and resuspended in PBS containing 0.1% BSA. Cells were incubated on ice with the appropriate antibody for 20 min and then washed. Samples were analyzed on a FACScaliber (BD Biosciences, Mountain View, Calif.). Background staining was assessed by use of an isotype control antibody.

Results

As a first step, the reactivity of 91 TILS from 26 melanoma patients was determined by measuring IFN-γ secretion following co-incubation of the TILs with autologous melanoma. Using the clinical threshold of 200 pg/ml IFN-γ, 39 TIL cultures were determined as reactive and 52 as nonreactive (Different TILs from the same patient produced different reactivity levels). The immune subpopulation compositions of these cultures were characterized by multicolor flow cytometry. Each triple staining of three different receptors X, Y and Z resulted in 6 single staining ($X^+$, $X^-$, $Y^+$, $Y^-$, $Z^+$, $Z^-$), 12 double staining (e.g. $X^+Y$) and 8 triple staining (e.g. $X^+Y^+Z$). The single, double and triple staining produces a hierarchy of subpopulation characterization ranging from general to more specific subpopulations. A quality control filtering procedure was employed yielding a final dataset containing 33 distinct subpopulations (see FIGS. 5-9 for filtering and dataset description).

Example 2

Comparison Between Individual Subpopulation Fractions and Use Thereof to Predict Reactive and Nonreactive TILs Materials and Methods SVM Classification:

SVM classifications were performed with the gist-train-svm software www.bioinformatics.ubc.ca/gist/. All classifications were performed with a linear kernel and input data was normalized by rescaling the columns to values between −1 and 1. All tests were conducted by applying a 'leave three out' procedure. SVM performance was evaluated by the ROC (receive operating characteristics) analysis which calculates the true positive rate versus True negative rate for different cutoffs. The ROC value namely the area under A ROC curve was reported for each test. In addition, the total accuracy (TA), sensitivity (SN), specificity (SP) and the Matthews correlation coefficient (CC) were calculated.

The present inventors compared individual subpopulation fractions and used them to predict reactive and nonreactive TILs (FIG. 2). The classification accuracy yielded a Matthews correlation coefficients (MCC) ranging from 0 to 0.58 and total accuracy ranging from 40% to 78%. In general, the discriminative power of individual subpopulations characterized by triple staining was superior to that of a single and double staining, which may be attributed to the better characterization of identity or functional state of the first compared to the later. For example, a $CD8^+$ marker is an indicator of cytotoxic activity while $CD8^+CD28^-CD152^-$ is, in addition to being cytotoxic, also fully activated and bearing no CD152 inhibitory receptors. This analysis emphasizes the limited predictive power of individual subpopulations.

To examine whether the combination of multiple subpopulations improves the prediction accuracy a support vector machine (SVM) model [W. S. Noble, Nat. Biotechnol. 24, 1565 (2006)] was applied.

Predicting TIL Reactivity Using an SVM Model:

Briefly, each TIL was mapped to a point in a multi-dimensional space according to its subpopulation constituents. The SVM classifier generates a hyper-surface that separates instances of the two classes. All classifications were done with a linear kernel and input data was normalized by rescaling the columns to values between −1 and 1. The classification was tested by applying a 'leave one out' procedure. SVM performance was evaluated using the Matthews correlation coefficient (MCC):

$$MCC = \frac{TP \cdot TN - FP \cdot FN}{\sqrt{(TP+FN)(TP+FP)(TN+FN)(TN+FP)}} \qquad \text{formula I}$$

where TP, FP, TN, FN are true positives, false positives, true negatives and false negatives respectively. The total accuracy (TA), sensitivity (SN), specificity (SP) and the ROC (receiver operating characteristics) values were also used. To optimize SVM classification a recursive feature elimination procedure was used. In each iteration the 10% of the least predictive features were removed, as determined by the error bound. Four different training sets were analyzed: single, double and triple staining features and the filtered training set (see FIG. 9). As a quality check d an additional run of the filtered training set was performed in which a group of 10 random features was included. The feature elimination rate of the subpopulation features was slower compared to the random features indicating that the former are informative of TIL reactivity.

The final SVM classifier contained the minimal feature subset that displayed the maximal MCC value. The optimal SVM with MCC=0.74 had eight parameters: $CD69^+$, $CD4^+CD69^-CD33^+$, $CD8^+CD28^-CD152^-$, $CD8^+CD85^-CD94^-$, $CD8^+CD69^-CD33^+$, $CD8^+CD69^+CD33^-$, $CD8^+CD69^-CD33^-$, $CD8^+CD69^+CD33^-$.

Some of the TIL samples in this study belong to a same patient. To exclude the possibility of interdependences between the samples that may cause a bias in the prediction a Bootstrapping control was performed. A leave five out procedure, 10,000 itarations was performed. The results were similar to the SVM testing. SVM classifications were performed with the gist software www.bioinformatics.ubc.ca/gist/.

In summary, the prediction accuracy of the SVM model was MCC=0.74 (87% total accuracy) compared to an MCC=0.58 (total accuracy 78%) achieved by the best individual subpopulation.

These results demonstrate the advantage of combining different subpopulation fractions for reactivity prediction and are in accordance with the "multi-player" nature of the immune system. The SVM had 13% misclassifications that may be explained by flow cytometry sensitivity limitations, important subpopulations that were not measured and the inherent stochasticity of the system. The fact that a high accuracy of prediction can be achieved by the SVM indicates that there is an underlying pattern connecting between the subpopulation fractions and the ultimate TIL reactivity.

Example 3

Use of Subpopulation Signatures to Predict TIL Reactivity

Results

Since the SVM model does not lend itself easily to biological interpretation, the present inventors decided to investigate the underlying biological rational that governs TIL reactivity. The usage of differential expression signatures has become a well established method for distinguishing between various cellular states and different pathological conditions. This concept was applied to cell populations, by using a similar notion of "subpopulations signature" that can be used to differentiate between reactive and nonreactive TILs (see FIG. 3A and FIG. 11). Each column corresponds to a TIL culture and the rows represent subpopulations. Two significant clusters emerge, each representing a profile of $CD4^+$ and $CD8^+$ enriched subsets. These two markers represent regulatory and cytotoxic T-cell subpopulations respectively (FIG. 1B). Interestingly, the two clusters also separate between nonreactive and reactive TILs (Fischer exact $P<10^{-3}$). This suggests that TIL reactivity against melanoma is largely dictated by its subpopulation composition. It was also observed that the nonreactive cluster is further divided into two sub-clusters, both of which are enriched with nonreactive TILs that have distinct profiles. The first is mostly $CD4^+$ while the other is a mixture of $CD8^+$ and $CD4^+$ subpopulation derivatives, suggesting $CD4^+$ dominance over $CD8^+$. To further simplify the subpopulation signature a decision tree algorithm was used that produced a simple set of rules for distinguishing between reactive and nonreactive TILs (FIG. 3B). The accuracy of these rule based predictions are 89% with MCC=0.79. These rules highlight three subpopulations, namely: $CD8^+CD28^-CD152^-$, $CD94^+$ and $CD8^+CD69^+CD33$. The first emphasizes the role of the CD28 and 152 receptors in determining the TIL reactivity in addition to $CD8^+$. Specifically, the present observation that reactive $CD8^+$ T-cells lack both co-stimulatory CD28 receptor and the co-inhibitory receptor CD152 on their surface is in agreement with current knowledge. CD28 tend to become down regulated and internalized following proper T-cell activation [S. C. Eck, D. Chang, A. D. Wells, L. A. Turka, Transplantation 64, 1497 (1997); P. S. Linsley, J. Bradshaw, M. Umes, L. Grosmaire, J. A. Ledbetter, J. Immunol. 150, 3161 (1993)]. The absence of CD152 receptor on reactive TILs is in accordance with its potent co-inhibitory role [M. L. Alegre, K. A. Frauwirth, C. B. Thompson, Nat. Rev. Immunol. 1, 220 (2001)]. The second subpopulation is marked by $CD94^+$, an inhibitory receptor expressed in low levels on T-cells [P. J. Leibson, Curr. Opin. Immunol. 16, 328 (2004)]. Its inhibitory function may explain why higher levels of it are correlated with nonreactive TILs. The third subpopulation ($CD8^+CD69^+CD33^-$) is characterized by the $CD69^+$ and $CD33^-$ receptor staining Little is known about the function of these two receptors. The present findings suggest that this subpopulation has a yet unknown role in determining T-cell functionality.

Example 4

Use of Subpopulation Analysis to Predict the Exact Level of IFN-γ Secretion

To test whether subpopulation analysis can be used, not only to classify between reactive and nonreactive TILs, but also to predict the exact level of IFN-γ secretion, attention was focused exclusively on the reactive TILs. To this end a linear regression was performed on pairs of subpopulations and IFN-γ levels. By using an equation of the form IFN-γ=$\alpha$+$\beta_1 \cdot X_1 + \beta_2 \cdot X_2$ where $X_1$ and $X_2$ represent the fraction of two different subpopulations it was possible to accurately determine the exact levels of IFN-γ with $P<10^{-4}$ (see FIG. 3C). The pair that yielded optimal results, in terms of IFN-γ secretion was $CD8^+CD28^-$ and $CD8^+CD69^+CD33^-$. Notably, these subpopulations are similar to those used for classification between reactive and nonreactive TILs in the decision tree (FIG. 3B).

Overall, these results indicate that TIL anti-tumor reactivity is too complex to be explained by an individual subpopulation or receptor. Yet, the combination of a few subpopulations based rules and simple formulas can explain the reactivity to a large extent.

Example 5

Controlling the Reactivity of TILs by Manipulation of their Subpopulation Fractions These observations raise the conjecture whether one could control reactivity of TILs by manipulating their subpopulation fractions. To test this hypothesis nonreactive associated subpopulations were selectively depleted.

Materials and Methods

T cell depletion was performed by incubating the TILs with anti-CD4 and/or anti-CD28 and/or anti-CD152 and/or anti-CD85 and/or anti-CD94 for 20 minutes. Subsequently, cells were mixed with anti mouse IgG coated magnetic beads (Dynal, Lake Success, N.Y.) for an additional 10 minutes, followed by magnetic depletion for 5 minutes. The negative fraction was then washed 3 times with cold PBS 0.1% BSA and was incubated for 36 hours at 37° C.

Results

The receptors used for depleting these subpopulations were CD4, CD28, CD85, CD94 and CD152. The experiments were performed on 12 nonreactive fresh TIL cultures that originated from four different melanoma patients (Table 6, herein below) and were not part of the 91 TIL samples used for the subpopulation signature elucidation. Reactivity levels, in terms of IFN-γ secretion, were measured. TILs with IFN-γ levels that exceeded 200 pg/ml were determined as reactive and otherwise as nonreactive (marked with a '+' and '−' respectively).

TABLE 6

| Patient | TIL | Reactive after separation |
|---|---|---|
| 1 | 1 | + |
|   | 2 | − |
| 2 | 1 | + |
|   | 2 | − |
|   | 3 | + |
|   | 4 | + |
|   | 5 | − |
| 3 | 1 | + |
| 4 | 1 | + |
|   | 2 | + |
|   | 3 | + |
|   | 4 | + |

First the subpopulation frequencies of each TIL were determined. Then, the inhibitory related subpopulations were depleted using magnetic bead negative selection. After 36 hours of recovery both original and manipulated TILs were challenged with autologous melanoma for 12 hours followed by supernatant IFN-γ measurement. Remarkably, 9 of the 12 originally nonreactive TILs became reactive after manipulation (FIG. 4A). The IFN-γ level of the 9 reactive TILs exceeded the 200 pg/ml clinical threshold with levels ranging between 300-4000 pg/ml (a 1.5 to 20 fold increase above the threshold). Two of the three TILs that retained a nonreactive state after manipulation also exhibited an increase in IFN-γ levels. As a negative control specificity and spontaneous release of IFN-γ secretion was tested by incubating the TILs with unrelated melanoma or culture media. In all controls IFN-γ levels remained below threshold indicating specificity and low spontaneous release (see FIG. 4A).

The fact that nonreactive TILs could be transformed into reactive ones suggests that nonreactivity is largely dictated by simple subpopulation interactions rather than lack of specificity to melanoma cancer epitopes.

In order to link the change in reactivity with the change in the underlying subpopulation composition, TIL profiles were examined prior and after the manipulation (see FIG. 4B). For this analysis 10 of the 12 TILs were used that had sufficient cell counts. The profile of 9 of the remaining 10 TILs prior to manipulation was similar to that of the nonreactive TILs as determined by the original 91 sample dataset (compare FIG. 3A and FIG. 4B). It can be seen that the shift from nonreactive to reactive state is accompanied by a transformation of subpopulation signature as indicated by blue arrows in FIG. 4B. This shift in profiles is further illustrated in FIG. 4C.

Understanding and predicting the output of a heterogeneous cell population is a highly challenging task with many biological and clinical implications. In this study multi-parametric modeling was used that is based on subpopulation fractions in order to accurately predict the reactivity levels of TILs, an example of an immune heterogeneous cell population. The present results show that although the number of possible subpopulation combinations is infinite, in practice TILs fall into a few distinct profiles, which may be defined as "subpopulations signatures". These findings were further simplified into a set of rules that map between subpopulation proportions and TIL reactivity. Guided by these rules specific subpopulations were selected for enrichment and depletion and the present inventors were able to transform nonreactive TILs into reactive ones. This approach may be applied in order to optimize the ACT clinical protocol by studying and manipulating TILs in the context of an objective clinical response. This general framework demonstrates the practical implications of systems biology in the context of clinical research and can be further extended to predict, understand and control cell population functions in fields such as stem cells, tumor immunology and tissue engineering.

What is claimed is:

1. A method of predicting responsiveness to autologous adoptive cell transfer therapy in a subject having metastatic melanoma, the method comprising contacting tumor infiltrating lymphocytes (TILs) of a tumor sample isolated from the subject with an antibody which recognizes CD8, an antibody which recognizes CD28 and an antibody which recognizes CD152 so as to determine a frequency of TILs having a CD8+CD28−CD152− signature, wherein a frequency of TILs having said CD8+CD28-CD152− signature below 25% is predicative of a negative responsiveness to autologous adoptive cell transfer therapy.

2. The method of claim 1, further comprising analyzing a frequency of TILs having a CD8+CD69+CD33− signature in the tumor sample of the subject, wherein a frequency of TILs having said CD8+CD69+CD33− signature above 60% and a CD8+CD28−CD152− signature above 45% is predicative of a negative responsiveness to autologous adoptive cell transfer therapy.

3. The method of claim 1, further comprising analyzing a frequency of TILs having a CD94+ signature in the sample, wherein a frequency of TILs having said CD8+CD28−CD152− signature below 25%, whilst having a CD94+ signature above 0.7% is further indicative of a negative responsiveness to adoptive cell transfer therapy.

* * * * *